US006692748B2

(12) United States Patent
Haldeman et al.

(10) Patent No.: US 6,692,748 B2
(45) Date of Patent: Feb. 17, 2004

(54) ADIPOCYTE COMPLEMENT RELATED PROTEIN ZACRP3X2 AND NUCLEIC ACIDS ENCODING ZACRP3X2

(75) Inventors: Betty A. Haldeman, Seattle, WA (US); Edward C. Thayer, Seattle, WA (US); Paul O. Sheppard, Granite Falls, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 10/012,605

(22) Filed: Dec. 7, 2001

(65) Prior Publication Data

US 2003/0104602 A1 Jun. 5, 2003

Related U.S. Application Data

(60) Provisional application No. 60/254,019, filed on Dec. 7, 2000.

(51) Int. Cl.[7] .................. A61K 39/00; C12N 15/09; C07K 14/715

(52) U.S. Cl. ................... 424/185.1; 424/192.1; 530/351; 530/350; 536/23.5; 435/320.1; 435/325; 435/69.1; 435/69.7

(58) Field of Search ............... 536/23.5; 530/350, 530/351; 435/320.1, 325, 69.1, 69.7; 424/185.1, 192.1

(56) References Cited

U.S. PATENT DOCUMENTS 6,521,233 B1  2/2003  Piddington et al.

FOREIGN PATENT DOCUMENTS

| EP | 1067182 | 1/2001 |
|---|---|---|
| WO | 99/06551 | 2/1999 |
| WO | 99/59618 | 11/1999 |
| WO | 00/56889 | 9/2000 |
| WO | 00/60080 | 10/2000 |
| WO | 00/63377 | 10/2000 |
| WO | 01/49728 | 7/2001 |
| WO | 01/54472 | 8/2001 |
| WO | 01/55173 | 8/2001 |
| WO | 02/04600 | 1/2002 |
| WO | 02/46417 | 6/2002 |

OTHER PUBLICATIONS

Maeda et al., *The Journal of Biological Chemistry*, 276(5):3628–3634 (2001).
Fruebis et al., *Proc. Natl. Acad. Sci. USA.*, 98(4): 2005–2010 (Feb. 13, 2001).
Wilson, *Washu–Merck EST Project*, 1995, Accession#R61191.
Wilson, *Washu–Merck EST Project*, 1995, Accession#R61190.
Wilson, *Washu–Merck EST Project*, 1995, Accession#H144663.
Wilson, *Washu–Merck EST Project*, 1995, Accession#H86570.
Marra, *WashU–HHM1 Mouse EST Project*, 1996, Accession#AA068843.
Marra, *WashU–HHM1 Mouse EST Project*, 1996, Accession#W82768.
Marra, *WashU–HHM1 Mouse EST Project*, 1996, Accession#W64775.
Wilson, *WashU–Merck EST Project*, 1996, Accession#AA055231.
Wilson, *WashU–Merck EST Project*, 1996, Accession#AA025306.
Wilson, *WashU–Merck EST Project*, 1996, Accession#AA024548.
Wilson, *WashU–Merck EST Project*, 1996, Accession#AA025644.
Marra, *WashU–HAM1 Mouse EST Project*, 1997, Accession#AA637749.
Strausberg, *NCI Cancer Genome Anatomy Project*, 1997, Accession#AA527298.
Wilson, *WashU–NCI Human EST Project*, 1997, Accession#AA663060.
Wilson, *WashU–NCI Human EST Project*, 1997, Accession#AA621679.
Wilson, *WashU–NCI Human EST Project*, 1997, Accession#AA224157.
Kerlavage, *TIGR EST*, 1997, Accession#AA332783.
Kerlavage, *TIGR EST*, 1997, Accession#AA334609.
Kerlavage, *TIGR EST*, 1997, Accession#AA322403.
*TIGR Tenative Human Consensus Sequence*, 1997, Accession#THC_H14463.
*TIGR Tenative Human Consensus Sequence*, 1997, Accession#THC_THC135435.
*TIGR Tenative Human Consensus Sequence*, 1997, Accession#THC_R61190.
*TIGR Tenative Human Consensus Sequence*, 1997, Accession#THC_AA024548.
*TIGR Tenative Human Consensus Sequence*, 1997, Accession#THC_THC160583.
*TIGR Tenative Human Consensus Sequence*, 1997, Accession#THC_THC167672.
Marra, *WashU–HHMI Mouse EST Project*, 1998, Accession#AA821459.
Strausberg, *NCI, Cancer Genome Anatomy Project*, 1998, Accession#AI265978.
Strausberg, *NCI, Cancer Genome Anatomy Project*, 1998, Accession#AI265976.

(List continued on next page.)

Primary Examiner—Lorraine Spector
Assistant Examiner—Eileen B. O'Hara
(74) Attorney, Agent, or Firm—Brian J. Walsh

(57) ABSTRACT

Novel zacrp3x2 polypeptides, polynucleotides encoding the polypeptides, and related compositions and methods are disclosed. Also disclosed are antibodies to the zacrp3x2 protein or fragments thereof.

11 Claims, No Drawings

OTHER PUBLICATIONS

Strausberg, *NCI, Cancer Genome Anatomy Project*, 1998, Accession#AI265984.
Strausberg, *NCI, Cancer Genome Anatomy Project*, 1998, Accession#AI265980.
Strausberg, *NCI, Cancer Genome Anatomy Project*, 1998, Accession#AI299699.
Strausberg, *NCI, Cancer Genome Anatomy Project*, 1998, Accession#AI193311.
Strausberg, *NCI, Cancer Genome Anatomy Project*, 1998, Accession#AI128115.
Strausberg, *NCI, Cancer Genome Anatomy Project*, 1998, Accession#AI123712.
Strausberg, *NCI, Cancer Genome Anatomy Project*, 1998, Accession#AI024632.
Strausberg, *NCI, Cancer Genome Anatomy Project*, 1998, Accession#AI078403.
Strausberg, *NCI, Cancer Genome Anatomy Project*, 1998, Accession#AI023643.
Strausberg, *NCI, Cancer Genome Anatomy Project*, 1998, Accession#AA992802.
Strausberg, *NCI, Cancer Genome Anatomy Project*, 1998, Accession#AA992463.
Strausberg, *NCI, Cancer Genome Anatomy Project*, 1998, Accession#AA826548.
Strausberg, *NCI, Cancer Genome Anatomy Project*, 1998, Accession#AA768490.
Strausberg, *NCI, Cancer Genome Anatomy Project*, 1998, Accession#AA747951.
Strausberg, *NCI, Cancer Genome Anatomy Project*, 1999, Accession#AI393787.
Marra, *WashU–NCI Mouse EST Project*, 1999, Accession#AI527737.
Marra, *WashU–NCI Mouse EST Project*, 1999, Accession#AI425863.
Marra, *WashU–NCI Mouse EST Project*, 1999, Accession#AI430561.

ADIPOCYTE COMPLEMENT RELATED PROTEIN ZACRP3X2 AND NUCLEIC ACIDS ENCODING ZACRP3X2

REFERENCE TO RELATED APPLICATION

This application is related to Provisional Application U.S. 60/254,019, filed on Dec. 7, 2000. Under 35 U.S.C. §119 (e)(1), this application claims benefit of said Provisional Application.

BACKGROUND OF THE INVENTION

Cell-cell and cell-extracellular matrix interactions allow for exchange of information between, and coordination among, various cells of a multi-cellular organism and are fundamental for most biological processes. These interactions play a role in everything from fertilization to death. Such interactions are essential during development and differentiation and are critical for the function and protection of the organism. For example, interaction between the cell and its environment is necessary to initiate and mediate tissue remodeling. Tissue remodeling may be initiated, for example, in response to many factors including physical injury, cytotoxic injury, metabolic stress or developmental stimuli. Modulation between pathology and healing (or metabolic optimization) may be done, in part, by the interaction of stimulated cells with the extracellular matrix as well as the local solvent.

The adipocyte complement related protein family plays a role in the interaction of cells with their environment, and appear to act at the interface of the extracellular matrix and the cell. These proteins include, Acrp30 (Scherer et al., *J. Biol. Chem.* 270:26746–49, 1995), apM1 (Maeda et al., *Biochem. Biophys. Res. Comm.* 221:286–9, 1996), GBP28 (Nakano et al., *J. Biochem.* 120:803–12, 1996), zsig39 (Sheppard and Humes, WIPO Published Patent No: WO99/10492), zsig37 (Sheppard, WIPO Published Patent No: WO99/04000), ZCRP30R1 (Smith et al., WIPO Published Patent No. WO99/56619), ACRP30R1L (Hensley et al., WIPO Published Patent No: WO99/59618), ACRP30R2 (Hensley et al., WIPO Published Patent No: WO99/64629), PRO 353 and PRO 344 (Wood et al., WIPO Published Patent No. WO99/28462), zacrp2 (Piddington et al., WO 00/63376), zacrp3 (Piddington et al., WO 00/63377), zacrp4 (Piddington et al., WO 01/02565), zacrp5 (Piddington et al., WO 00/73444), zacrp6 (Piddington et al., WO 00/73466), zacrp11 (Piddington et al., WO 00/**), and zacrp12 (Piddington et al., WO 00/**).

These proteins all share a collagen-like domain comprising perfect Gly-Xaa-Pro and imperfect Gly-Xaa-Xaa collagen repeats, and a C1q domain. Complement factor C1q consists of six copies of three related polypeptides (A, B and C chains), with each polypeptide being about 225 amino acids long with a near amino-terminal collagen domain and a carboxy-terminal globular region. Six triple helical regions are formed by the collagen domains of the six A, six B and six C chains, forming a central region and six stalks. A globular head portion is formed by association of the globular carboxy terminal domain of an A, a B and a C chain. C1q is composed of six globular heads linked via six collagen-like stalks to a central fibril region. Sellar et al., *Biochem. J.* 274: 481–90, 1991. This configuration is often referred to as a bouquet of flowers. Acrp30 has a similar bouquet structure formed from a single type of polypeptide chain. The C1q globular domain of ACRP30 has been determined to have a 10 beta strand "jelly roll" topology (Shapiro and Scherer, *Curr. Biol.* 8:335–8, 1998). The structural elements such as folding topologies, conserved residues and similar trimer interfaces and intron positions are homologous to the tumor necrosis factor family suggesting a link between the TNF and C1q families.

In addition, injury to the blood vessels sets in motion a series of events to repair the damage and control release of blood from the vessel. This process is known as hemostasis. Platelets play an early role in hemostasis by forming a thrombus or plug to temporarily repair the vessel damage. Platelets normally do not interact with the endothelium lining the vessel walls, but injury to blood vessels, through accident or during surgical procedures, may disrupt endothelial cells. Depending on the extent of the injury, various subendothelial elements such as collagens, elastic lamina or smooth muscle cells with associated fibrillar collagens will be exposed to the flowing blood.

When the subendothelium is exposed following vessel injury, platelets moving in the local blood flow interact with exposed subendothelium matrix containing collagen and are slowed down. Further interaction between receptors on the platelet surface and the exposed collagen layer leads to platelet binding and activation resulting in the arrest of local blood flow. The bound platelets are activated and form aggregates with platelets in the passing blood flow through the formation of fibrinogen-interplatelet bridges (Moroi and Jung, *Frontiers in Bioscience* 3:719–28, 1998; Barnes et al., *Atherosclerosis XI*, Jacotot et al., eds., Elsevier Science, pp. 299–306, 1998 and Barnes et al., *Curr. Opin. Hematol.* 5:314–20, 1998).

The hemostatic response is graded and dependent on the degree of injury to the blood vessel, the specific blood vessels constituents exposed and the blood flow conditions in the injured area (Rand et al., *Thrombosis and Haemostasis* 78:445–50, 1997). Exposure of the subendothelium matrix (type VI collagen and von Willebrand factor), such as during mild vascular injury, promotes a low degree of adhesion and aggregation in areas with low blood flow conditions. Injuries that result in a greater degree of vascular trauma and exposure of additional vascular constituents, such as the internal elastic lamina and elastin-associated microfibrils, will stimulate the formation of stronger platelet aggregates. Severe vascular trauma, exposing fibril collagens, provokes a thrombotic platelet response, which protects the victim from excessive loss of blood (Rand et al., ibid.).

Complement factor C1q consists of six copies of three related polypeptides (A, B and C chains), with each polypeptide being about 225 amino acids long with a near amino-terminal collagen domain and a carboxy-terminal globular region. Six triple helical regions are formed by the collagen domains of the six A, six B and six C chains, forming a central region and six stalks. A globular head portion is formed by association of the globular carboxy terminal domain of an A, a B and a C chain. C1q is therefore composed of six globular heads linked via six collagen-like stalks to a central fibril region. Sellar et al., *Biochem. J.* 274: 481–90, 1991. This configuration is often referred to as a bouquet of flowers. Acrp30 has a similar bouquet structure formed from a single type of polypeptide chain.

C1q has been found to stimulate defense mechanisms as well as trigger the generation of toxic oxygen species that can cause tissue damage (Tenner, *Behring Inst. Mitt.* 93:241–53, 1993). C1q binding sites are found on platelets. Additionally complement and C1q play a role in inflammation. The complement activation is initiated by binding of C1q to immunoglobulins.

Proteins that play a role in cellular interaction, such as transcription factors and hormones are useful diagnostic and therapeutic agents. Proteins that mediate specific interactions, such a remodeling, would be particularly useful. Moreover, inhibitors of hemostasis would be useful for to increase blood flow following vascular injury and to pacify collagenous surfaces. Inhibitors of Clq and the complement pathway would be useful for anti-inflammatory applications, inhibition of complement activation and thrombotic activity.

The present invention provides such polypeptides for these and other uses that should be apparent to those skilled in the art from the teachings herein.

DESCRIPTION OF THE INVENTION

The present invention provides a novel adipocyte complement related protein, designated "zacrp3x2". The present invention also provides "zacrp3x2" variant polypeptides and "zacrp3x2" fusion proteins, as well as nucleic acid molecules encoding such polypeptides and proteins, and methods for using these nucleic acid molecules and amino acid sequences.

Within one aspect, the present invention provides an isolated polypeptide comprising SEQ ID NO:2. In one embodiment, the isolated polypeptide disclosed above is covalently linked at the amino or carboxyl terminus to a moiety selected from the group consisting of affinity tags, toxins, radionucleotides, enzymes and fluorophores. In another embodiment, the isolated polypeptide disclosed above is in combination with a pharmaceutically acceptable vehicle.

Within a second aspect, the present invention provides an a fusion protein comprising a first portion and a second portion joined by a peptide bond, said first portion consisting of a polypeptide selected from the group consisting of: a) a polypeptide consisting of amino acid residues 23–186 of SEQ ID NO:2; and b) a polypeptide consisting of amino acid residues 23–319 of SEQ ID NO:2; and said second portion comprising another polypeptide.

Within another aspect, the present invention provides an antibody or antibody fragment that specifically binds to a polypeptide as disclosed above. In one embodiment, the antibody is as disclosed above, wherein said antibody is selected from the group consisting of: (a) polyclonal antibody; (b) murine monoclonal antibody; (c) humanized antibody derived from b); (d) an antibody fragment; and (e) human monoclonal antibody. In one embodiment, the antibody fragment is as disclosed above, wherein said antibody fragment is selected from the group consisting of F(ab'), F(ab), Fab', Fab, Fv, scFv, and minimal recognition unit.

Within another aspect, the present invention provides an anti-idiotype antibody that specifically binds to said antibody as disclosed above.

Within another aspect, the present invention provides an isolated nucleic acid molecule encoding a polypeptide of SEQ ID NO:2.

Within another aspect, the present invention provides an isolated nucleic acid molecule selected from the group consisting of: a) a nucleic acid molecule of SEQ ID NO:1; and b) a nucleic acid molecule of SEQ ID NO:7.

Within another aspect, the present invention provides an isolated polynucleotide encoding a fusion protein comprising a first portion and a second portion joined by a peptide bond, said first portion is selected from the group consisting of: a) a polypeptide consisting of amino acid residues 23–186 of SEQ ID NO:2; and b) a polypeptide consisting of amino acid residues 23–319 of SEQ ID NO:2; and said second portion comprising another polypeptide.

Within another aspect, the present invention provides an expression vector comprising the following operably linked elements: a transcription promoter; a DNA segment encoding a polypeptide as disclosed above; and a transcription terminator.

Within another aspect, the present invention provides a cultured cell into which has been introduced an expression vector as disclosed above, wherein said cell expresses said polypeptide encoded by said DNA segment.

Within another aspect, the present invention provides a method of producing a polypeptide comprising: culturing a cell into which has been introduced an expression vector as disclosed above; whereby said cell expresses said polypeptide encoded by said DNA segment; and recovering said expressed polypeptide.

The present invention provides nucleic acid molecules that encode a novel adipocyte complement related protein, designated as "zacrp3x2." An illustrative nucleotide sequence that encodes zacrp3x2 is provided by SEQ ID NO:1. The encoded polypeptide has the amino acid sequence of SEQ ID NO:2. Thus, the zacrp3x2 gene described herein encodes a polypeptide of 319 amino acids, as shown in SEQ ID NO:2.

An illustrative polypeptide is a polypeptide that comprises the amino acid sequence of SEQ ID NO:2.

The present invention further provides antibodies and antibody fragments that specifically bind with such polypeptides. Exemplary antibodies include polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. The present invention further includes compositions comprising a carrier and a peptide, polypeptide, or antibody described herein.

The present invention also provides isolated nucleic acid molecules that encode a zacrp3x2 polypeptide, wherein the nucleic acid molecule is selected from the group consisting of: a nucleic acid molecule having the nucleotide sequence of SEQ ID NO:4; a nucleic acid molecule encoding the amino acid sequence of SEQ ID NO:2; and a nucleic acid molecule that remains hybridized following stringent wash conditions to a nucleic acid molecule consisting of a nucleotide sequence selected from the group consisting of: (a) the nucleotide sequence of SEQ ID NO:4, (b) the nucleotide encoding the polypeptide of SEQ ID NO:2, and (c) a nucleotide sequence that is the complement of the nucleotide sequence of (a) or (b).

The present invention further contemplates an isolated nucleic acid molecule that comprise the nucleotide sequence of SEQ ID NO:1.

The present invention also includes vectors and expression vectors comprising such nucleic acid molecules. Such expression vectors may comprise a transcription promoter, and a transcription terminator, wherein the promoter is operably linked with the nucleic acid molecule, and wherein the nucleic acid molecule is operably linked with the transcription terminator. The present invention further includes recombinant host cells comprising these vectors and expression vectors. Illustrative host cells include bacterial, yeast, fungal, insect, mammalian, and plant cells. Recombinant host cells comprising such expression vectors can be used to produce zacrp3x2 polypeptides by culturing such recombinant host cells that comprise the expression vector and that produce the zacrp3x2 protein, and, optionally, isolating the zacrp3x2 protein from the cultured recombinant host cells.

The present invention also contemplates methods for detecting the presence of zacrp3×2 RNA in a biological sample, comprising the steps of (a) contacting a zacrp3×2 nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of SEQ ID NO:1, or its complement, and (b) detecting the formation of hybrids of the nucleic acid probe and either the test RNA molecules or the synthesized nucleic acid molecules, wherein the presence of the hybrids indicates the presence of zacrp3×2 RNA in the biological sample. An example of a biological sample is a human biological sample, such as a biopsy or autopsy specimen.

The present invention further provides methods for detecting the presence of zacrp3×2 polypeptide in a biological sample, comprising the steps of: (a) contacting the biological sample with an antibody or an antibody fragment that specifically binds with a polypeptide having the amino acid sequence of SEQ ID NO:2, wherein the contacting is performed under conditions that allow the binding of the antibody or antibody fragment to the biological sample, and (b) detecting any of the bound antibody or bound antibody fragment. Such an antibody or antibody fragment may further comprise a detectable label selected from the group consisting of radioisotope, fluorescent label, chemiluminescent label, enzyme label, bioluminescent label, and colloidal gold. An exemplary biological sample is a human biological sample.

The present invention also provides kits for performing these detection methods. For example, a kit for detection of zacrp3×2 gene expression may comprise a container that comprises a nucleic acid molecule, wherein the nucleic acid molecule is selected from the group consisting of (a) a nucleic acid molecule comprising the nucleotide sequence of SEQ ID NO:1, (b) a nucleic acid molecule comprising the complement of the nucleotide sequence of SEQ ID NO:1, (c) a nucleic acid molecule that is a fragment of (a) consisting of at least eight nucleotides, and (d) a nucleic acid molecule that is a fragment of (b) consisting of at least eight nucleotides. Illustrative nucleic acid molecules include nucleic acid molecules comprising nucleotides 56 to 136 179 to 448, or 56 to 448 of SEQ ID NO:1, or the complement thereof. Such a kit may also comprise a second container that comprises one or more reagents capable of indicating the presence of the nucleic acid molecule. On the other hand, a kit for detection of zacrp3×2 protein may comprise a container that comprises an antibody, or an antibody fragment, that specifically binds with a polypeptide having the amino acid sequence of SEQ ID NO:2.

These and other aspects of the invention will become evident upon reference to the following detailed description. In addition, various references are identified below and are incorporated by reference in their entirety.

Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., (α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either contain segments of nucleic acid combined and juxtaposed in an arrangement not existing in nature.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces zacrp3×2 from an expression vector. In contrast, zacrp3×2 can be produced by a cell that is a "natural source" of zacrp3×2, and that lacks an expression vector.

A "fusion protein" is a hybrid protein expressed by a nucleic acid molecule comprising nucleotide sequences of at least two genes. For example, a fusion protein can comprise at least part of a zacrp3×2 polypeptide fused with a polypeptide that binds an affinity matrix. Such a fusion protein provides a means to isolate large quantities of zacrp3×2 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a nucleotide sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-zacrp3×2 antibody, and thus, an anti-idiotype antibody mimics an epitope of zacrp3×2.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-zacrp3×2 monoclonal antibody fragment binds with an epitope of zacrp3×2.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). Nucleic acid molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a therapeutic agent. Examples of therapeutic agents suitable for such fusion proteins include immunomodulators ("antibody-immunomodulator fusion protein") and toxins ("antibody-toxin fusion protein").

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for zacrp3×2" or an "zacrp3×2 anti-sense oligonucleotide" is an oligonucleotide having a sequence (a) capable of forming a stable triplex with a portion of the zacrp3×2 gene, or (b) capable of forming a stable duplex with a portion of an mRNA transcript of the zacrp3×2 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant zacrp3×2 gene" refers to nucleic acid molecules that encode a polypeptide having an amino acid sequence that is a modification of SEQ ID NO:2. Such variants include naturally-occurring polymorphisms of zacrp3×2 genes, as well as synthetic genes that contain conservative amino acid substitutions of the amino acid sequence of SEQ ID NO:2. Additional variant forms of zacrp3×2 genes are nucleic acid molecules that contain insertions or deletions of the nucleotide sequences described herein. A variant zacrp3×2 gene can be identified by determining whether the gene hybridizes with a nucleic acid molecule having the nucleotide sequence of SEQ ID NO:1, or its complement, under stringent conditions.

Alternatively, variant zacrp3×2 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123–151 (CRC Press, Inc. 1997), and Bishop (ed.), *Guide to Human Genome Computing*, 2nd Edition (Academic Press, Inc. 1998)). Particular methods for determining sequence identity are described below.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation. "Paralogs" are distinct but structurally related proteins made by an organism. Paralogs are believed to arise through gene duplication. For example, ($\alpha$-globin, $\beta$-globin, and myoglobin are paralogs of each other.

The present invention includes functional fragments of zacrp3×2 genes. Within the context of this invention, a "functional fragment" of a zacrp3×2 gene refers to a nucleic acid molecule that encodes a portion of a zacrp3×2 polypeptide which specifically binds with an anti-zacrp3×2 antibody. For example, a functional fragment of a zacrp3×2 gene described herein comprises a portion of the nucleotide sequence of SEQ ID NO:1, and encodes a polypeptide that specifically binds with an anti-zacrp3×2 antibody.

Due to the imprecision of standard analytical methods, molecular weights and lengths of polymers are understood to be approximate values. When such a value is expressed as "about" X or "approximately" X, the stated value of X will be understood to be accurate to ±10%.

The present invention is based in part upon the discovery of a novel DNA sequence that encodes a polypeptide having homology to the adipocyte complement related protein family. The polypeptide has been designated zacrp3×2. The nucleotide sequence of zacrp3×2 is described in SEQ ID NO:1, and its deduced amino acid sequence is described in SEQ ID NO:2. The zacrp3×2 polypeptide includes a signal sequence, comprising amino acid 1 (Met) to amino acid residue 22 (Cys) of SEQ ID NO:2, nucleotides 1–66 of SEQ ID NO:1. The mature polypeptide ranges from amino acid 23 (Gln) to amino acid 319 (Lys) of SEQ ID NO:2, nucleotides 67–957 of SEQ ID NO:1. Within the mature polypeptide is an N-terminal region of no known homology, between amino acid residue 23 (Gln) and 123 (Arg) of SEQ ID NO:2, nucleotides 67–369 of SEQ ID NO:1. In addition is found a collagen-like domain between amino acid 124 (Gly) and 186 (Pro) of SEQ ID NO:2, nucleotides 370–558 of SEQ ID NO:1. In the collagen-like domain there are 21 collagen repeats, six perfect Gly-Xaa-Pro repeats and fifteen imperfect Gly-Xaa-Xaa repeats. Intra-chain disulfide bonding may involve the cysteines at amino acid residues 39, 42, and 43 of SEQ ID NO:2. Proline residues found in this domain at amino acid residue 128, 129, 131, 132, 134, 135, 138, 167, 176, 183, and 186 of SEQ ID NO:2 may be hydroxylated. The zacrp3×2 polypeptide also includes a carboxy-terminal Clq/TNF domain, between amino acid 187 (Pro) to 319 (Lys) of SEQ ID NO:2, nucleotides 559–957 of SEQ ID NO:1. An aromatic motif F-X(5)-[ND]-X(4)-[FYWL]-X(6)-F-X(5)-G-X-Y-X(4) (SEQ ID NO:8) is also found within this domain between residues 210 (Phe) and 240 (Phe) of SEQ ID NO:2, nucleotides 628–720 of SEQ ID NO:1. X represents any amino acid residue and the number in parentheses ( ) indicates the amino acid number of residues. The amino acid residues contained within the square parentheses [ ] restrict the choice of amino acid residues at that particular position. There is a fair amount of conserved structure within the Clq domain to enable proper folding.

Zacrp3x2 appears to be a splice variant of the adipocyte complement related protein zacrp3 (Piddington and Sheppard, WIPO International Publication No. WO 00/63377, Oct. 26, 2000). Comparing the amino acid sequences of zacrp3x2 (SEQ ID NO:2) and zacrp3 (SEQ ID NO:3), zacrp3x2 contains a 73 amino acid residue insert (SEQ ID NO:4) between amino acid residues 28 and 29 of SEQ ID NO:3. The 3' sequence of zacrp3x2 (SEQ ID NO:5) was cloned and used to generate a contig that contained the remainder of the 5' sequence. The cDNA encoding a full length zacrp3x2 polypeptide of SEQ ID NO:2 is provided in SEQ ID NO:1.

The 73 amino acid insert of zacrp3x2 relative to zacrp3, which precedes the collagen domain, is reminiscent of other protein family members such as EDA (Ectodermal Dysplasia Protein) (SEQ ID NO:6). EDA has an extended N-terminal region followed by a collagen domain and a TNF-like globular domain. EDA is involved in the development of sweat glands and hair. EDA has pro region splice variants which are differentially expressed in developing tissues. The differential expression and alternatively spliced pro-region of zacrp3x2 suggests different roles in mature and developing tissues. Zacrp3x2 may modulate development of substructures of, for example, liver, breast, brain, lymph tissue, and/or uterus. Zacrp3x2 may also be useful in augmenting tissue repair and development. The zacrp3x2 protein, or fragments thereof, may modulate the zacrp3-like activity by altering the multimerization state, or receptor binding characteristics of zacrp3 or zacrp3x2. Thus another aspect of the invention includes n-terminal fragments of zacrp3x2 ranging from 1(Met) or 23(gln) to 123(Arg) of SEQ ID NO:2.

Another aspect of the present invention includes zacrp3x2 polypeptide fragments. Preferred fragments include those containing the collagen-like domain of zacrp3x2 polypeptides, ranging from amino acid 1 (Met), 23 (Gln), or 124 (Gly) to amino acid 186 (Pro) of SEQ ID NO:2, a portion of the zacrp3x2 polypeptide containing the collagen-like domain or a portion of the collagen-like domain capable of dimerization or oligomerization. As used herein the term "collagen" or "collagen-like domain" refers to a series of repeating triplet amino acid sequences, "repeats" or "collagen repeats" represented by the motifs Gly-Xaa-Pro or Gly-Xaa-Xaa, where Xaa is any amino acid reside. The number of collagen repeats within a collagen-like domain varies within the adipocyte complement related protein family. Fragments or proteins containing such collagen-like domains may form homomeric constructs (dimers or oligomers of the same fragment or protein). Moreover, such fragments or proteins containing such collagen-like domains may form heteromeric constructs (dimers, trimers or oligomers of different fragments or proteins).

These fragments are particularly useful in the study of collagen dimerization or oligomerization or in formation of fusion proteins as described more fully below. Polynucleotides encoding such fragments are also encompassed by the present invention, including the group consisting of (a) polynucleotide molecule comprising a sequence of nucleotides as shown in SEQ ID NO:1 from nucleotide 1, 67, or 370 to nucleotide 558; (b) polynucleotide molecules that encode a zacrp3x2 polypeptide fragment that is at least 80%, 90%, or 95% identical to the amino acid sequence of SEQ ID NO:2 from amino acid residue 124 (Gly) to amino acid residue 186 (Pro); (c) molecules complementary to (a) or (b); and (d) degenerate nucleotide sequences encoding a zacrp3x2 polypeptide collagen-like domain fragment.

Other preferred fragments include the globular Clq domain of zacrp3x2 polypeptides, ranging from amino acid 187 (Pro) to 319 (Lys) of SEQ ID NO:2, a portion of the zacrp3x2 polypeptide containing the Clq domain or an active portion of the Clq domain. Other Clq domain containing proteins include Clq A, B and C (Sellar et al., ibid., Reid, ibid., and Reid et al., 1982, ibid), chipmunk hibernation-associated plasma proteins HP-20, HP-25 and HP-27 (Takamatsu et al., ibid and Kondo & Kondo, ibid), human precerebellin (Urade et al., ibid), human endothelial cell multimerin (Hayward et al., ibid), vertebrate collagens type VIII and X (Muragaki et al., ibid), adipocyte complement related proteins Acrp30 (Scherer et al., ibid), apM1 (Maeda et al., ibid), GBP28 (Nakano et al., ibid), zsig39 (Sheppard and Humes, WIPO Published Patent No: WO99/10492), zsig37 (Sheppard, WIPO Published Patent No: WO99/04000), ZCRP30R1 (Smith et al., WIPO Published Patent No. WO99/56619), ACRP30R1L (Hensley et al., WIPO Published Patent No: WO99/59618), ACRP30R2 (Hensley et al., WIPO Published Patent No: WO99/64629), PRO 353 and PRO 344 (Wood et al., WIPO Published Patent No. WO99/28462), zacrp2 (Piddington et al., WO 00/63376), zacrp3 (Piddington et al., WO 00/63377), zacrp4 (Piddington et al., WO 01/02565), zacrp5 (Piddington et al., WO 00/73444), zacrp6 (Piddington et al., WO 00/73466), zacrp11 (Piddington et al., WO 00/**), and zacrp12 (Piddington et al., WO 00/**).

The Clq domain of zacrp3x2 contains 10 beta-strand "jelly roll" topology (amino acid residues 192–196, 213–215, 221–224, 228–231, 234–246, 248–255, 263–270, 273–285, 290–295, and 309–314 of SEQ ID NO:2). These strands are designated "A", "A'", "B", "B'", "C", "D", "E", "F", "G" and "H" respectively (Shapiro and Scherer, *Curr. Biol.* 8:335–8, 1998).

Zacrp3x2 has two receptor binding loops, at amino acid residues 184 (Gly)-212 (Ser) and 243 (Met)-255 (Leu) of SEQ ID NO:2. Those skilled in the art will recognize that these boundaries are approximate, and are based on alignments with known proteins and predictions of protein folding. The core receptor binding region is predicted to include amino acid residues 197 (Leu)-223 (Val) and 254 (Tyr)-270 (Met) of SEQ ID NO:2. Amino acid residues 234 (Gly), 236 (Tyr), 285 (Leu) and 307 (Phe) appear to be conserved across the superfamily.

These fragments are particularly useful in the study or modulation of energy balance or neurotransmission, particularly diet- or stress-related neurotransmission, collagen inhibition, and complement inhibition. Anti-microbial activity may also be present in such fragments. The homology of adipocyte complement related protein Clq domains to TNF proteins (Shapiro and Scherer, ibid) suggests such fragments would be useful in obesity-related insulin resistance, immune regulation, inflammatory response, platelet adhesion modulation, apoptosis and osteoclast maturation. Polynucleotides encoding such fragments are also encompassed by the present invention, including the group consisting of (a) polynucleotide molecules comprising a sequence of nucleotides as shown in SEQ ID NO:1 from nucleotide 559 to nucleotide 957; (b) polynucleotide molecules that encode a zacrp3×2 polypeptide fragment that is at least 80%, 90%, or 95% identical to the amino acid sequence of SEQ ID NO:2 from amino acid residue 187 (Pro) to amino acid residue 319 (Lys); (c) molecules complementary to (a) or (b); and (d) degenerate nucleotide sequences encoding a zacrp3×2 polypeptide Clq domain fragment.

Other zacrp3×2 polypeptide fragments of the present invention include both the collagen-like domain and the Clq domain ranging from amino acid residue 23 (Gln), or 124 (Gly) to 319 (Lys) of SEQ ID NO:2. Polynucleotides encoding such fragments are also encompassed by the present invention, including the group consisting of (a) polynucleotide molecules comprising a sequence of nucleotides as shown in SEQ ID NO:1 from nucleotide 67 or 370 to nucleotide 957; (b) polynucleotide molecules that encode a zacrp3×2 polypeptide fragment that is at least 80%, 90%, or 95% identical to the amino acid sequence of SEQ ID NO:2 from amino acid residue 23 (Gln), or 124 (Gly) to 319 (Lys) of SEQ ID NO:2; (c) molecules complementary to (a) or (b); and (d) degenerate nucleotide sequences encoding a zacrp3×2 polypeptide collagen-like domain-Clq domain fragment.

Production of a Human zacrp3×2 Gene

Nucleic acid molecules encoding a human zacrp3×2 gene can be obtained by screening a human cDNA or genomic library using polynucleotide probes based upon SEQ ID NO:1. These techniques are standard and well-established. As an illustration, a nucleic acid molecule that encodes a human zacrp3×2 gene can be isolated from a human cDNA library. In this case, the first step would be to prepare the cDNA library using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Short Protocols in Molecular Biology*, $3^{rd}$ *Edition*, pages 4–1 to 4–6 (John Wiley & Sons 1995) ["Ausubel (1995)"]; Wu et al., *Methods in Gene Biotechnology*, pages 33–41 (CRC Press, Inc. 1997) ["Wu (1997)"]). Alternatively, total RNA can be isolated by extracting ground tissue with guanidinium isothiocyanate, extracting with organic solvents, and separating RNA from contaminants using differential centrifugation (see, for example, Chirgwin et al., *Biochemistry* 18:52 (1979); Ausubel (1995) at pages 4–1 to 4–6; Wu (1997) at pages 33–41).

In order to construct a cDNA library, poly(A)$^+$ RNA must be isolated from a total RNA preparation. Poly(A)$^+$ RNA can be isolated from total RNA using the standard technique of oligo(dT)-cellulose chromatography (see, for example, Aviv and Leder, *Proc. Nat'l Acad. Sci. USA* 69:1408 (1972); Ausubel (1995) at pages 4–11 to 4–12).

Double-stranded cDNA molecules are synthesized from poly(A)$^+$ RNA using techniques well-known to those in the art. (see, for example, Wu (1997) at pages 41–46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λgt11," in *DNA Cloning: A Practical Approach Vol. I*, Glover (ed.), page 49 (IRL Press, 1985); Wu (1997) at pages 47–52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.).

To amplify the cloned cDNA molecules, the cDNA library is inserted into a prokaryotic host, using standard techniques. For example, a cDNA library can be introduced into competent *E. coli* DH5 cells, which can be obtained, for example, from Life Technologies, Inc. (Gaithersburg, Md.).

A human genomic library can be prepared by means well-known in the art (see, for example, Ausubel (1995) at pages 5–1 to 5–6; Wu (1997) at pages 307–327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5–1 to 5–6; Wu (1997) at pages 307–327).

Nucleic acid molecules that encode a human zacrp3×2 gene can also be obtained using the polymerase chain reaction (PCR) with oligonucleotide primers having nucleotide sequences that are based upon the nucleotide sequences of the zacrp3×2 gene, as described herein. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), pages 211–215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), pages 317–337 (Humana Press, Inc. 1993).

Alternatively, human genomic libraries can be obtained from commercial sources such as Research Genetics (Huntsville, Ala.) and the American Type Culture Collection (Manassas, Va.).

A library containing cDNA or genomic clones can be screened with one or more polynucleotide probes based upon SEQ ID NO:1, using standard methods (see, for example, Ausubel (1995) at pages 6–1 to 6–11).

Anti-zacrp3×2 antibodies, produced as described below, can also be used to isolate DNA sequences that encode human zacrp3×2 genes from cDNA libraries. For example, the antibodies can be used to screen λgt11 expression libraries, or the antibodies can be used for immunoscreening following hybrid selection and translation (see, for example, Ausubel (1995) at pages 6–12 to 6–16; Margolis et al., "Screening λ expression libraries with antibody and protein probes," in *DNA Cloning 2: Expression Systems, 2nd Edition*, Glover et al. (eds.), pages 1–14 (Oxford University Press 1995)).

As an alternative, a zacrp3×2 gene can be obtained by synthesizing nucleic acid molecules using mutually priming long oligonucleotides and the nucleotide sequences described herein (see, for example, Ausubel (1995) at pages 8—8 to 8–9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263–268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

One method for building a synthetic gene requires the initial production of a set of overlapping, complementary oligonucleotides, each of which is between 20 to 60 nucleotides long. The sequences of the strands are planned so that, after annealing, the two end segments of the gene are aligned to give blunt ends. Each internal section of the gene has complementary 3' and 5' terminal extensions that are designed to base pair precisely with an adjacent section. Thus, after the gene is assembled, the only remaining requirement to complete the process is to seal the nicks along the backbones of the two strands with T4 DNA ligase. In addition to the protein coding sequence, synthetic genes can be designed with terminal sequences that facilitate insertion into a restriction endonuclease sites of a cloning vector and other sequences should also be added that contain signals for the proper initiation and termination of transcription and translation.

An alternative way to prepare a full-size gene is to synthesize a specified set of overlapping oligonucleotides (40 to 100 nucleotides). After the 3' and 5' extensions (6 to 10 nucleotides) are annealed, large gaps still remain, but the base-paired regions are both long enough and stable enough to hold the structure together. The duplex is completed and the gaps filled by enzymatic DNA synthesis with *E. coli* DNA polymerase I. This enzyme uses the 3'-hydroxyl groups as replication initiation points and the single-stranded regions as templates. After the enzymatic synthesis is completed, the nicks are sealed with T4 DNA ligase. For larger genes, the complete gene sequence is usually assembled from double-stranded fragments that are each put together by joining four to six overlapping oligonucleotides (20 to 60 base pairs each). If there is a sufficient amount of the double-stranded fragments after each synthesis and annealing step, they are simply joined to one another. Otherwise, each fragment is cloned into a vector to amplify the amount of DNA available. In both cases, the double-stranded constructs are sequentially linked to one another to form the entire gene sequence. Each double-stranded fragment and the complete sequence should be characterized by DNA sequence analysis to verify that the chemically synthesized gene has the correct nucleotide sequence. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l. Acad. Sci. USA* 87:633 (1990).

The sequence of a zacrp3×2 cDNA or zacrp3×2 genomic fragment can be determined using standard methods. Zacrp3×2 polynucleotide sequences disclosed herein can also be used as probes or primers to clone 5' non-coding regions of a zacrp3×2 gene. Promoter elements from a zacrp3×2 gene can be used to direct the expression of heterologous genes in, for example, transgenic animals or patients undergoing gene therapy. The identification of genomic fragments containing a zacrp3×2 promoter or regulatory element can be achieved using well-established techniques, such as deletion analysis (see, generally, Ausubel (1995)).

Cloning of 5' flanking sequences also facilitates production of zacrp3×2 proteins by "gene activation," as disclosed in U.S. Pat. No. 5,641,670. Briefly, expression of an endogenous zacrp3×2 gene in a cell is altered by introducing into the zacrp3×2 locus a DNA construct comprising at least a targeting sequence, a regulatory sequence, an exon, and an unpaired splice donor site. The targeting sequence is a zacrp3×2 5' non-coding sequence that permits homologous recombination of the construct with the endogenous zacrp3×2 locus, whereby the sequences within the construct become operably linked with the endogenous zacrp3×2 coding sequence. In this way, an endogenous zacrp3×2 promoter can be replaced or supplemented with other regulatory sequences to provide enhanced, tissue-specific, or otherwise regulated expression.

Production of zacrp3×2 Gene Variants

The present invention provides a variety of nucleic acid molecules, including DNA and RNA molecules, that encode the zacrp3×2 polypeptides disclosed herein. Those skilled in the art will readily recognize that, in view of the degeneracy of the genetic code, considerable sequence variation is possible among these polynucleotide molecules. SEQ ID NO:7 is a degenerate nucleotide sequence that encompasses all nucleic acid molecules that encode the zacrp3×2 polypeptide of SEQ ID NO:2. Those skilled in the art will recognize that the degenerate sequence of SEQ ID NO:7 also provides all RNA sequences encoding SEQ ID NO:2, by substituting U for T. Thus, the present invention contemplates zacrp3×2 polypeptide-encoding nucleic acid molecules comprising nucleotides 1 to 957 of SEQ ID NO:1, and their RNA equivalents.

Table 1 sets forth the one-letter codes used within SEQ ID NO:7 to denote degenerate nucleotide positions. "Resolutions" are the nucleotides denoted by a code letter. "Complement" indicates the code for the complementary nucleotide (s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:7, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

Different species can exhibit "preferential codon usage." In general, see, Grantham et al., *Nuc. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (see Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:7 serves as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are zacrp3x2 polypeptides from other mammalian species, including porcine, ovine, bovine, canine, feline, equine, and other primate polypeptides. Such orthologs of zacrp3x2 can be cloned using information and compositions provided by the present invention in combination with conventional cloning techniques. For example, a cDNA can be cloned using mRNA obtained from a tissue or cell type that expresses zacrp3x2 as disclosed herein. Suitable sources of mRNA can be identified by probing northern blots with probes designed from the sequences disclosed herein. A library is then prepared from mRNA of a positive tissue or cell line.

A zacrp3x2-encoding cDNA can then be isolated by a variety of methods, such as by probing with a complete or partial cDNA or with one or more sets of degenerate probes based on the disclosed sequences. A cDNA can also be cloned using the polymerase chain reaction with primers designed from the representative zacrp3×2 sequences disclosed herein. Within an additional method, the cDNA library can be used to transform or transfect host cells, and expression of the cDNA of interest can be detected with an antibody to zacrp3×2 polypeptide. Similar techniques can also be applied to the isolation of genomic clones.

Those skilled in the art will recognize that the sequence disclosed in SEQ ID NO:1 represents a single allele of human zacrp3×2, and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO:1, including those containing silent mutations and those in which mutations result in amino acid sequence changes, are within the scope of the present invention, as are proteins which are allelic variants of SEQ ID NO:2. cDNA molecules generated from alternatively spliced mRNAs, which retain the properties of the zacrp3×2 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:1, to nucleic acid molecules consisting of the nucleotide sequence of SEQ ID NO:1, or to nucleic acid molecules consisting of a nucleotide sequence complementary to SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the $T_m$ of the hybrid and a hybridization buffer having up to 1 M Na$^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20–70° C. and a hybridization buffer containing up to 6×SSC and 0–50% formamide. A higher degree of stringency can be achieved at temperatures of from 40–70° C. with a hybridization buffer having up to 4×SSC and from 0–50% formamide. Highly stringent conditions typically encompass temperatures of 42–70° C. with a hybridization buffer having up to 1×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software, as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_m$ or 5–10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxyuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a Na⁺ source, such as SSC (1×SSC:0.15 M sodium chloride, 15 mM sodium citrate) or SSPE (1×SSPE:1.8 M NaCl, 10 mM NaH$_2$PO$_4$, 1 mM EDTA, pH 7.7). By decreasing the ionic concentration of the buffer, the stability of the hybrid is increased. Typically, hybridization buffers contain from between 10 mM–1 M Na⁺. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant zacrp3×2 polypeptide can be hybridized with a nucleic acid molecule having the nucleotide sequence of SEQ ID NO:1 (or its complement) at 42° C. overnight in a solution comprising 50% formamide, 5×SSC (1×SSC:0.15 M sodium chloride and 15 mM sodium citrate), 50 mM sodium phosphate (pH 7.6), 5× Denhardt's solution (100× Denhardt's solution:2% (w/v) Ficoll 400, 2% (w/v) polyvinylpyrrolidone, and 2% (w/v) bovine serum albumin, 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant zacrp3×2 polypeptide remained hybridized following stringent washing conditions with a nucleic acid molecule having the nucleotide sequence of SEQ ID NO:1 (or its complement), in which the wash stringency is equivalent to 0.5×–2×SSC with 0.1% SDS at 55–65° C., including 0.5×SSC with 0.1% SDS at 55° C., or 2×SSC with 0.1% SDS at 65° C. One of skill in the art can readily devise equivalent conditions, for example, by substituting the SSPE for SSC in the wash solution.

Typical highly stringent washing conditions include washing in a solution of 0.1×–0.2×SSC with 0.1% sodium dodecyl sulfate (SDS) at 50–65° C. In other words, nucleic acid molecules encoding a variant zacrp3×2 polypeptide remained hybridized following stringent washing conditions with a nucleic acid molecule having the nucleotide sequence of SEQ ID NO:1 (or its complement), in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

The present invention also provides isolated zacrp3×2 polypeptides that have a substantially similar sequence identity to the polypeptide of SEQ ID NO:2, or orthologs. The term "substantially similar sequence identity" is used herein to denote polypeptides having 70%, 80%, 90%, 95%, 96%, 97%, 98%, or 99% sequence identity to the sequence shown in SEQ ID NO:2.

The present invention also contemplates zacrp3×2 variant nucleic acid molecules that can be identified using two criteria: a determination of the similarity between the encoded polypeptide with the amino acid sequence of SEQ ID NO:2, and a hybridization assay, as described above. Such zacrp3×2 variants include nucleic acid molecules (1) that remain hybridized following stringent washing conditions with a nucleic acid molecule having the nucleotide sequence of SEQ ID NO:1 (or its complement), in which the wash stringency is equivalent to 0.5×–2×SSC with 0.1% SDS at 55–65° C., and (2) that encode a polypeptide comprising the amino acid sequence amino acid residue 42 to amino acid residue 110 of SEQ ID NO:2.

Alternatively, zacrp3×2 variants can be characterized as nucleic acid molecules (1) that remain hybridized following highly stringent washing conditions with a nucleic acid molecule having the nucleotide sequence of SEQ ID NO:1 (or its complement), in which the wash stringency is equivalent to 0.1×–0.2×SSC with 0.1% SDS at 50–65° C., and (2) that encode a polypeptide comprising the amino acid sequence amino acid residue 42 to amino acid residue 250 of SEQ ID NO:2.

The present invention also includes particular zacrp3×2 variants are characterized using hybridization analysis with a reference nucleic acid molecule that is a fragment of a nucleic acid molecule consisting of the nucleotide sequence of SEQ ID NO:1, or its complement. For example, such reference nucleic acid molecules include nucleic acid molecules consisting of the following nucleotide sequences, or complements thereof, SEQ ID NO:1, nucleotides 169–795 of SEQ ID NO:1.

Percent sequence identity is determined by conventional methods. See, for example, Altschul et al., *Bull. Math. Bio.* 48:603 (1986), and Henikoff and Henikoff, *Proc. Nat'l Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |

TABLE 3-continued

|   | A  | R  | N  | D  | C  | Q  | E  | G  | H  | I  | L  | K  | M  | F  | P  | S  | T  | W  | Y | V |
|---|----|----|----|----|----|----|----|----|----|----|----|----|----|----|----|----|----|----|---|---|
| G | 0  | -2 | 0  | -1 | -3 | -2 | -2 | 6  |    |    |    |    |    |    |    |    |    |    |   |   |
| H | -2 | 0  | 1  | -1 | -3 | 0  | 0  | -2 | 8  |    |    |    |    |    |    |    |    |    |   |   |
| I | -1 | -3 | -3 | -3 | -1 | -3 | -3 | -4 | -3 | 4  |    |    |    |    |    |    |    |    |   |   |
| L | -1 | -2 | -3 | -4 | -1 | -2 | -3 | -4 | -3 | 2  | 4  |    |    |    |    |    |    |    |   |   |
| K | -1 | 2  | 0  | -1 | -3 | 1  | 1  | -2 | -1 | -3 | -2 | 5  |    |    |    |    |    |    |   |   |
| M | -1 | -1 | -2 | -3 | -1 | 0  | -2 | -3 | -2 | 1  | 2  | -1 | 5  |    |    |    |    |    |   |   |
| F | -2 | -3 | -3 | -3 | -2 | -3 | -3 | -3 | -1 | 0  | 0  | -3 | 0  | 6  |    |    |    |    |   |   |
| P | -1 | -2 | -2 | -1 | -3 | -1 | -1 | -2 | -2 | -3 | -3 | -1 | -2 | -4 | 7  |    |    |    |   |   |
| S | 1  | -1 | 1  | 0  | -1 | 0  | 0  | 0  | -1 | -2 | -2 | 0  | -1 | -2 | -1 | 4  |    |    |   |   |
| T | 0  | -1 | 0  | -1 | -1 | -1 | -1 | -2 | -2 | -1 | -1 | -1 | -1 | -2 | -1 | 1  | 5  |    |   |   |
| W | -3 | -3 | -4 | -4 | -2 | -2 | -3 | -2 | -2 | -3 | -2 | -3 | -1 | 1  | -4 | -3 | -2 | 11 |   |   |
| Y | -2 | -2 | -2 | -3 | -2 | -1 | -2 | -3 | 2  | -1 | -1 | -2 | -1 | 3  | -3 | -2 | -2 | 2  | 7 |   |
| V | 0  | -3 | -3 | -3 | -1 | -2 | -2 | -3 | -3 | 3  | 1  | -2 | 1  | -1 | -2 | -2 | 0  | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative zacrp3×2 variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with the amino acid sequence of SEQ ID NO:2. That is, variants can be obtained that contain one or more amino acid substitutions of SEQ ID NO:2, in which an alkyl amino acid is substituted for an alkyl amino acid in a zacrp3×2 amino acid sequence, an aromatic amino acid is substituted for an aromatic amino acid in a zacrp3×2 amino acid sequence, a sulfur-containing amino acid is substituted for a sulfur-containing amino acid in a zacrp3×2 amino acid sequence, a hydroxy-containing amino acid is substituted for a hydroxy-containing amino acid in a zacrp3×2 amino acid sequence, an acidic amino acid is substituted for an acidic amino acid in a zacrp3×2 amino acid sequence, a basic amino acid is substituted for a basic amino acid in a zacrp3×2 amino acid sequence, or a dibasic monocarboxylic amino acid is substituted for a dibasic monocarboxylic amino acid in a zacrp3×2 amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than -1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of zacrp3×2 are characterized by having greater than 96%, at least 97%, at least 98%, or at least 99% sequence identity to the corresponding amino acid sequence (e.g., SEQ ID NO:2), wherein the variation in amino acid sequence is due to one or more conservative amino acid substitutions.

Conservative amino acid changes in a zacrp3×2 gene can be introduced by substituting nucleotides for the nucleotides recited in SEQ ID NO:1. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8–10 to 8–22; and McPherson (ed.), *Directed Mutagenesis: A Practical Approach* (IRL Press 1991)).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethyl-cyteine, hydroxyethylhomocysteine, nitroglutamine, homoglutamine, pipecolic acid, thiazolidine carboxylic acid, dehydroproline, 3- and 4-methylproline, 3,3-dimethyl-proline, tert-leucine, norvaline, 2-azaphenylalanine, 3-azaphenylalanine, 4-azapheny-lalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in Xenopus oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for zacrp3×2 amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259–311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol.Chem.* 271:4699 (1996).

The location of zacrp3×2 activity domains can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992). Moreover, zacrp3×2 labeled with biotin or FITC can be used for expression cloning of zacrp3×2 substrates and inhibitors.

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)).

Variants of the disclosed zacrp3×2 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-zacrp3×2 antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of zacrp3×2 polypeptides and nucleic acid molecules encoding such functional fragments. Routine deletion analyses of nucleic acid molecules can be performed to obtain functional fragments of a nucleic acid molecule that encodes a zacrp3×2 polypeptide. As an illustration, DNA molecules having the nucleotide sequence of SEQ ID NO:1 can be digested with Bal31 nuclease to obtain a series of nested deletions. One alternative to exonuclease digestion is to use oligonucleotide-directed mutagenesis to introduce deletions or stop codons to specify production of a desired fragment. Alternatively, particular fragments of a zacrp3×2 gene can be synthesized using the polymerase chain reaction.

As an illustration, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2–5A synthetase induced by human interferon," in *Biological Interferon Systems, Proceedings of ISIR-TNO Meeting on Interferon Systems*, Cantell (ed.), pages 65–72 (Nijhoff 1987), Herschman, "The EGF Receptor," in *Control of Animal Cell Proliferation*, Vol. 1, Boynton et al., (eds.) pages 169–199 (Academic Press 1985), Coumailleau et al., *J. Biol. Chem.* 270:29270 (1995); Fukunaga et al., *J. Biol.Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a zacrp3x2 gene that has amino acid changes, compared with the amino acid sequence of SEQ ID NO:2. A variant zacrp3x2 gene can be identified on the basis of structure by determining the level of identity with nucleotide and amino acid sequences of SEQ ID NOs:1 and 2, as discussed above. An alternative approach to identifying a variant gene on the basis of structure is to determine whether a nucleic acid molecule encoding a potential variant zacrp3x2 gene can hybridize to a nucleic acid molecule having the nucleotide sequence of SEQ ID NO:1, as discussed above.

The present invention also provides polypeptide fragments or peptides comprising an epitope-bearing portion of a zacrp3x2 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides preferably contain at least four to ten amino acids, at least ten to fifteen amino acids, or about 15 to about 30 amino acids of SEQ ID NO:2. Such epitope-bearing peptides and polypeptides can be produced by fragmenting a zacrp3x2 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997).

For any zacrp3x2 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise zacrp3x2 variants based upon the nucleotide and amino acid sequences described herein. Accordingly, the present invention includes a computer-readable medium encoded with a data structure that provides at least one of SEQ ID NOs:1, 2, 3, 4, or 6. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

Production of Zacrp3x2 Fusion Proteins

Fusion proteins of zacrp3x2 can be used to express zacrp3x2 in a recombinant host, and to isolate expressed zacrp3x2. As described below, particular zacrp3x2 fusion proteins also have uses in diagnosis and therapy.

One type of fusion protein comprises a peptide that guides a zacrp3x2 polypeptide from a recombinant host cell. To direct a zacrp3x2 polypeptide into the secretory pathway of a eukaryotic host cell, a secretory signal sequence (also known as a signal peptide, a leader sequence, prepro sequence or pre sequence) is provided in the zacrp3x2 expression vector. While the secretory signal sequence may be derived from zacrp3x2, a suitable signal sequence may also be derived from another secreted protein or synthesized de novo. The secretory signal sequence is operably linked to a zacrp3x2-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

While the secretory signal sequence of zacrp3x2 or another protein produced by mammalian cells (e.g., tissue-type plasminogen activator signal sequence, as described, for example, in U.S. Pat. No. 5,641,655) is useful for expression of zacrp3x2 in recombinant mammalian hosts, a yeast signal sequence is preferred for expression in yeast cells. Examples of suitable yeast signal sequences are those derived from yeast mating pheromone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, $2^{nd}$ Edition, Glover and Hames (eds.), pages 123–167 (Oxford University Press 1995).

In bacterial cells, it is often desirable to express a heterologous protein as a fusion protein to decrease toxicity, increase stability, and to enhance recovery of the expressed protein. For example, zacrp3x2 can be expressed as a fusion protein comprising a glutathione S-transferase polypeptide. Glutathione S-transferase fusion proteins are typically soluble, and easily purifiable from *E. coli* lysates on immobilized glutathione columns. In similar approaches, a zacrp3x2 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, $2^{nd}$ Edition, Glover and Hames (Eds.), pages 15–58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyhistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

Another form of fusion protein comprises a zacrp3×2 polypeptide and an immunoglobulin heavy chain constant region, typically an $F_c$ fragment, which contains two constant region domains and a hinge region but lacks the variable region. As an illustration, Chang et al., U.S. Pat. No. 5,723,125, describe a fusion protein comprising a human interferon and a human immunoglobulin Fc fragment, in which the C-terminal of the interferon is linked to the N-terminal of the Fc fragment by a peptide linker moiety. An example of a peptide linker is a peptide comprising primarily a T cell inert sequence, which is immunologically inert. In such a fusion protein, an illustrative Fc moiety is a human γ4 chain, which is stable in solution and has little or no complement activating activity. Accordingly, the present invention contemplates a zacrp3×2 fusion protein that comprises a zacrp3×2 moiety and a human Fc fragment, wherein the C-terminus of the zacrp3×2 moiety is attached to the N-terminus of the Fc fragment via a peptide linker. The zacrp3×2 moiety can be a zacrp3×2 molecule or a fragment thereof.

In another variation, a zacrp3×2 fusion protein comprises an IgG sequence, a zacrp3×2 moiety covalently joined to the amino terminal end of the IgG sequence, and a signal peptide that is covalently joined to the amino terminal of the zacrp3×2 moiety, wherein the IgG sequence consists of the following elements in the following order: a hinge region, a $CH_2$ domain, and a $CH_3$ domain. Accordingly, the IgG sequence lacks a $CH_1$ domain. The zacrp3×2 moiety displays a zacrp3×2 activity, as described herein, such as the ability to bind with a zacrp3×2 antibody. This general approach to producing fusion proteins that comprise both antibody and nonantibody portions has been described by LaRochelle et al., EP 742830 (WO 95/21258).

Fusion proteins comprising a zacrp3×2 moiety and an Fc moiety can be used, for example, as an in vitro assay tool. For example, the presence of a zacrp3×2 inhibitor in a biological sample can be detected using a zacrp3×2-antibody fusion protein, in which the zacrp3×2 moiety is used to target the substrate or inhibitor, and a macromolecule, such as Protein A or anti-Fc antibody, is used to detect the bound fusion protein-receptor complex. Furthermore, such fusion proteins can be used to identify molecules that interfere with the binding of zacrp3×2 and a substrate.

Fusion proteins can be prepared by methods known to those skilled in the art by preparing each component of the fusion protein and chemically conjugating the components. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16–19 to 16–25.

zacrp3×2 Analogs and zacrp3×2 Inhibitors

One general class of zacrp3×2 analogs are variants having an amino acid sequence that is a mutation of the amino acid sequence disclosed herein. Another general class of zacrp3×2 analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype zacrp3×2 antibodies mimic zacrp3×2, these domains can provide zacrp3×2 activity. Methods of producing anti-idiotypic catalytic antibodies are known to those of skill in the art (see, for example, Joron et al., *Ann. N.Y. Acad. Sci.* 672:216 (1992), Friboulet et al., *Appl. Biochem. Biotechnol.* 47:229 (1994), and Avalle et al., *Ann. N.Y. Acad. Sci.* 864:118 (1998)).

Another approach to identifying zacrp3×2 analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

Solution in vitro assays can be used to identify a zacrp3×2 substrate or inhibitor. Solid phase systems can also be used to identify a substrate or inhibitor of a zacrp3×2 polypeptide. For example, a zacrp3×2 polypeptide or zacrp3×2 fusion protein can be immobilized onto the surface of a receptor chip of a commercially available biosensor instrument (BIACORE, Biacore AB; Uppsala, Sweden). The use of this instrument is disclosed, for example, by Karlsson, *Immunol. Methods* 145:229 (1991), and Cunningham and Wells, *J. Mol. Biol.* 234:554 (1993).

In brief, a zacrp3×2 polypeptide or fusion protein is covalently attached, using amine or sulfhydryl chemistry, to dextran fibers that are attached to gold film within a flow cell. A test sample is then passed through the cell. If a zacrp3×2 substrate or inhibitor is present in the sample, it will bind to the immobilized polypeptide or fusion protein, causing a change in the refractive index of the medium, which is detected as a change in surface plasmon resonance of the gold film. This system allows the determination on- and off-rates, from which binding affinity can be calculated, and assessment of the stoichiometry of binding, as well as the kinetic effects of zacrp3×2 mutation. This system can also be used to examine antibody-antigen interactions, and the interactions of other complement/anti-complement pairs.

Production of zacrp3×2 Polypeptides in Cultured Cells

The polypeptides of the present invention, including full-length polypeptides, functional fragments, and fusion proteins, can be produced in recombinant host cells following conventional techniques. To express a zacrp3×2 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a zacrp3×2 expression vector may comprise a zacrp3×2 gene and a secretory sequence derived from a zacrp3×2 gene or another secreted gene.

Zacrp3×2 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163–181 (John Wiley & Sons, Inc. 1996)).

Alternatively, a prokaryotic promoter, such as the bacteriophage T3 RNA polymerase promoter, can be used to control zacrp3×2 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. Preferably, the transfected cells are selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multidrug resistance, puromycin acetyltransferase) can also be used. Alternatively, markers that introduce an altered phenotype, such as green fluorescent protein, or cell surface proteins (e.g., CD4, CD8, Class I MHC, and placental alkaline phosphatase) may be used to sort transfected cells from untransfected cells by such means as FACS sorting or magnetic bead separation technology.

Zacrp3×2 polypeptides can also be produced by cultured cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. For example, adenovirus vector infected human 293 cells (ATCC Nos. CRL-1573, 45504, 45505) can be grown as adherent cells or in suspension culture at relatively high cell density to produce significant amounts of protein (see Garnier et al., *Cytotechnol.* 15:145 (1994)).

Zacrp3×2 genes may also be expressed in other higher eukaryotic cells, such as avian, fungal, insect, yeast, or plant cells. The baculovirus system provides an efficient means to introduce cloned zacrp3×2 genes into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the Drosophila metallothionein promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the zacrp3×2 polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed zacrp3×2 polypeptide, for example, a Glu-Glu epitope tag (Grussenmeyer et al., *Proc. Nat'l Acad. Sci.* 82:7952 (1985)). Using a technique known in the art, a transfer vector containing a zacrp3×2 gene is transformed into *E. coli*, and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed which replace the native zacrp3×2 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native zacrp3×2 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as Drosophila Schneider-2 cells, and the HIGH FIVEO cell line (Invitrogen) derived from Trichoplusia ni (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the T. ni cells. When recombinant virus is used, the cells are typically grown up from an inoculation density of approximately $2$–$5 \times 10^5$ cells to a density of $1$–$2 \times 10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147–168 (The Humana Press, Inc. 1991), by Patel et al., "The baculovirus expression system," in *DNA Cloning 2: Expression Systems, 2nd Edition*, Glover et al.(eds.), pages 205–244 (Oxford University Press 1995), by Ausubel (1995) at pages 16–37 to 16–57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183–218 (John Wiley & Sons, Inc. 1996).

Fungal cells, including yeast cells, can also be used to express the genes described herein. Yeast species of particular interest in this regard include *Saccharomyces cerevisiae, Pichia pastoris,* and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides there from are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). An illustrative vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. An illustrative selectable marker for use in *Pichia methanolica* is a *P. methanolica* ADE2 gene, which encodes phosphoribosyl-5-aminoimidaole carboxylase (AIRC; EC 4.1.1.21), and which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67–88 (CRC Press, 1993).

Alternatively, zacrp3×2 genes can be expressed in prokaryotic host cells. Suitable promoters that can be used to express zacrp3×2 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of Bacillus, Streptomyces promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al.(1995).

Useful prokaryotic hosts include *E. coli* and *Bacillus subtilis*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilis* include BR151, YB886, MI119, MI120, and B170 (see, for example, Hardy, "Bacillus Cloning Methods," in *DNA Cloning: A Practical Approach*, Glover (ed.) (IRL Press 1985)).

When expressing a zacrp3×2 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995). General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59–92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology* Volume 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Isolation of zacrp3×2 Polypeptides

The polypeptides of the present invention can be purified to at least about 80% purity, to at least about 90% purity, to at least about 95% purity, or greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. Certain purified polypeptide preparations are substantially free of other polypeptides, particularly other polypeptides of animal origin.

Fractionation and/or conventional purification methods can be used to obtain preparations of zacrp3×2 purified from natural sources, and recombinant zacrp3×2 polypeptides and fusion zacrp3×2 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in zacrp3×2 isolation and purification can be devised by those of skill in the art. For example, anti-zacrp3×2 antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification.

Zacrp3×2 polypeptides or fragments thereof may also be prepared through chemical synthesis, as described above. Zacrp3×2 polypeptides may be monomers or multimers; glycosylated or non-glycosylated; PEGylated or non-PEGylated; and may or may not include an initial methionine amino acid residue.

The present invention also contemplates chemically modified zacrp3×2 compositions, in which a zacrp3×2 polypeptide is linked with a polymer. Typically, the polymer is water soluble so that the zacrp3×2 conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-(C1–C10) alkoxy, or aryloxy derivatives thereof (see, for example, Harris, et al., U.S. Pat. No. 5,252,714). The polymer may be branched or unbranched. Moreover, a mixture of polymers can be used to produce zacrp3×2 conjugates.

Zacrp3×2 conjugates used for therapy should preferably comprise pharmaceutically acceptable water-soluble polymer moieties. Suitable water-soluble polymers include polyethylene glycol (PEG), monomethoxy-PEG, mono-(C1–C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A zacrp3×2 conjugate can also comprise a mixture of such water-soluble polymers. Anti-zacrp3×2 antibodies or anti-idiotype antibodies can also be conjugated with a water-soluble polymer.

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

Peptides and polypeptides of the present invention comprise at least six, at least nine, or at least 15 contiguous amino acid residues of SEQ ID NO:2. Within certain embodiments of the invention, the polypeptides comprise 20, 30, 40, 50, 100, or more contiguous residues of these amino acid sequences. Additional polypeptides can comprise at least 15, at least 30, at least 40, or at least 50 contiguous amino acids of such regions of SEQ ID NO:2. Nucleic acid molecules encoding such peptides and polypeptides are useful as polymerase chain reaction primers and probes.

Production of Antibodies to Zacrp3×2 Proteins

Antibodies to zacrp3×2 can be obtained, for example, using as an antigen the product of a zacrp3×2 expression vector or zacrp3×2 isolated from a natural source. Particularly useful anti-zacrp3×2 antibodies "bind specifically" with zacrp3×2. Antibodies are considered to be specifically binding if the antibodies exhibit at least one of the following two properties: (1) antibodies bind to zacrp3×2 with a threshold level of binding activity, and (2) antibodies do not significantly cross-react with polypeptides related to zacrp3×2.

With regard to the first characteristic, antibodies specifically bind if they bind to a zacrp3×2 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect zacrp3×2, but not known related polypeptides using a standard Western blot analysis. Examples of known related polypeptides are orthologs and proteins from the same species that are members of a protein family.

Anti-zacrp3x2 antibodies can be produced using antigenic zacrp3x2 epitope-bearing peptides and polypeptides. Antigenic epitope-bearing peptides and polypeptides of the present invention contain a sequence of at least nine, preferably between 15 to about 30 amino acids contained within SEQ ID NO:2. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with zacrp3x2. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in zacrp3x2 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), is first used to identify amino acid sequences representing areas of greatest local hydrophilicity (parameter: seven residues averaged). In the second step, Emini's method, Emini et al., *J. Virology* 55:836 (1985), is used to calculate surface probabilities (parameter: surface decision threshold (0.6)=1). Third, the Karplus-Schultz method, Karplus and Schultz, *Naturwissenschaften* 72:212 (1985), is used to predict backbone chain flexibility (parameter: flexibility threshold (0.2)=1). In the fourth and fifth steps of the analysis, secondary structure predictions are applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549–586 (Plenum Press 1990), and Garnier-Robson, Garnier et al., *J. Mol. Biol.* 120:97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors are combined to determine a surface contour value, designated as the "antigenic index." Finally, a peak broadening function is applied to the antigenic index, which broadens major surface peaks by adding 20, 40, 60, or 80% of the respective peak value to account for additional free energy derived from the mobility of surface regions relative to interior regions. This calculation is not applied, however, to any major peak that resides in a helical region, since helical regions tend to be less flexible.

Polyclonal antibodies to recombinant zacrp3x2 protein or to zacrp3x2 isolated from natural sources can be prepared using methods well-known to those of skill in the art. Antibodies can also be generated using a zacrp3x2-glutathione transferase fusion protein, which is similar to a method described by Burrus and McMahon, *Exp. Cell. Res.* 220:363 (1995). General methods for producing polyclonal antibodies are described, for example, by Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995).

The immunogenicity of a zacrp3x2 polypeptide can be increased through the use of an adjuvant, such as alum (aluminum hydroxide) or Freund's complete or incomplete adjuvant. Polypeptides useful for immunization also include fusion polypeptides, such as fusions of zacrp3x2 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horse, cow, dog, chicken, rat, mouse, rabbit, goat, guinea pig, or sheep, an anti-Zacrp3x2 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-zacrp3x2 antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1–2.6.7 (John Wiley & Sons 1991) ["Coligan"], Picksley et al., "Production of monoclonal antibodies against proteins expressed in *E. coli*," in *DNA Cloning 2: Expression Systems*, 2nd Edition, Glover et al.(eds.), page 93 (Oxford University Press 1995)).

Briefly, monoclonal antibodies can be obtained by injecting mice with a composition comprising a zacrp3x2 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-zacrp3x2 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology*, Vol. 10, pages 79–104 (The Humana Press, Inc. 1992)).

For particular uses, it may be desirable to prepare fragments of anti-zacrp3×2 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of V$_H$ and V$_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise V$_H$ and V$_L$ chains which are connected by a peptide linker. These single-chain antigen binding proteins (scFv) are prepared by constructing a structural gene comprising DNA sequences encoding the V$_H$ and V$_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to zacrp3×2 polypeptide in vitro, and selecting antibody display libraries in phage or similar vectors (for instance, through use of immobilized or labeled zacrp3×2 protein or peptide). Genes encoding polypeptides having potential zacrp3×2 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zacrp3×2 sequences disclosed herein to identify proteins which bind to zacrp3×2.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-zacrp3×2 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice*, Cleland et al.(eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-zacrp3×2 antibodies or antibody fragments, using standard techniques. See, for example, Green et al., "Production of Polyclonal Antisera," in *Methods In Molecular Biology: Immunochemical Protocols*, Manson (ed.), pages 1–12 (Humana Press 1992). Also, see Coligan at pages 2.4.1–2.4.7. Alternatively, monoclonal anti-idiotype antibodies can be prepared using anti-zacrp3×2 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

Anti-idiotype zacrp3×2 antibodies, as well as zacrp3×2 polypeptides. can be used to identify and to isolate zacrp3×2 substrates and inhibitors. For example, proteins and peptides of the present invention can be immobilized on a column and used to bind substrate and inhibitor proteins from biological samples that are run over the column (Hermanson et al. (eds.), *Immobilized Affinity Ligand Techniques*, pages 195–202 (Academic Press 1992)). Radiolabeled or affinity labeled zacrp3×2 polypeptides can also be used to identify or to localize zacrp3×2 substrates and inhibitors in a biological sample (see, for example, Deutscher (ed.), *Methods in Enzymol.*, vol. 182, pages 721–37 (Academic Press 1990); Brunner et al., *Ann. Rev. Biochem.* 62:483 (1993); Fedan et al., *Biochem. Pharmacol.* 33:1167 (1984)).

Use of Zacrp3×2 Nucleotide Sequences to Detect Zacrp3×2 Gene Expression and to Examine Zacrp3×2 Gene Structure Nucleic acid molecules can be used to detect the expression of a zacrp3×2 gene in a biological sample. Such probe molecules include double-stranded nucleic acid molecules comprising the nucleotide sequence of SEQ ID NO:1, or a fragment thereof, as well as single-stranded nucleic acid molecules having the complement of the nucleotide sequence of SEQ ID NO:1, or a fragment thereof. Probe molecules may be DNA, RNA, oligonucleotides, and the like.

In a basic assay, a single-stranded probe molecule is incubated with RNA, isolated from a biological sample, under conditions of temperature and ionic strength that promote base pairing between the probe and target zacrp3×2 RNA species. After separating unbound probe from hybridized molecules, the amount of hybrids is detected.

Well-established hybridization methods of RNA detection include northern analysis and dot/slot blot hybridization (see, for example, Ausubel (1995) at pages 4–1 to 4–27, and Wu et al.(eds.), "Analysis of Gene Expression at the RNA Level," in *Methods in Gene Biotechnology*, pages 225–239 (CRC Press, Inc. 1997)). Nucleic acid probes can be detectably labeled with radioisotopes such as $^{32}P$ or $^{35}S$. Alternatively, zacrp3×2 RNA can be detected with a non-radioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemilumninescent substrates. Illustrative non-radioactive moieties include biotin, fluorescein, and digoxigenin.

Zacrp3×2 oligonucleotide probes are also useful for in vivo diagnosis. As an illustration, $^{18}F$-labeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

One variation of PCR for diagnostic assays is reverse transcriptase-PCR (RT-PCR). In the RT-PCR technique, RNA is isolated from a biological sample, reverse transcribed to cDNA, and the cDNA is incubated with zacrp3×2 primers (see, for example, Wu et al. (eds.), "Rapid Isolation of Specific cDNAs or Genes by PCR," in *Methods in Gene Biotechnology*, pages 15–28 (CRC Press, Inc. 1997)). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or zacrp3×2 anti-sense oligomers. Oligo-dT primers offer the advantage that various mRNA nucleotide sequences are amplified that can provide control target sequences. zacrp3×2 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled zacrp3×2 probe, and examined by autoradiography. Additional alternative approaches include the use of digoxigenin-labeled deoxyribonucleic acid triphosphates to provide chemiluminescence detection, and the C-TRAK calorimetric assay.

Another approach for detection of zacrp3×2 expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniques* 20:240 (1996)). Alternative methods for detection of zacrp3×2 sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161 (1996), Ehricht et al., *Eur. J. Biochem.* 243:358 (1997), and Chadwick et al., *J. Virol. Methods* 70:59 (1998)). Other standard methods are known to those of skill in the art.

Zacrp3×2 probes and primers can also be used to detect and to localize zacrp3×2 gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology*, pages 259–278 (CRC Press, Inc. 1997), and Wu et al. (eds.), "Localization of DNA or Abundance of mRNA by Fluorescence In Situ Hybridization (RISH)," in *Methods in Gene Biotechnology*, pages 279–289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)).

Zacrp3×2 nucleotide sequences can be used in linkage-based testing for various diseases, and to determine whether a subject's chromosomes contain a mutation in the zacrp3×2 gene. Detectable chromosomal aberrations at the zacrp3×2 gene locus include, but are not limited to, aneuploidy, gene copy number changes, insertions, deletions, restriction site changes and rearrangements. Of particular interest are genetic alterations that inactivate a zacrp3×2 gene. Aberrations associated with a zacrp3×2 locus can be detected using nucleic acid molecules of the present invention by employing molecular genetic techniques, such as restriction fragment length polymorphism (RFLP) analysis, short tandem repeat (STR) analysis employing PCR techniques, amplification-refractory mutation system analysis (ARMS), single-strand conformation polymorphism (SSCP) detection, RNase cleavage methods, denaturing gradient gel electrophoresis, fluorescence-assisted mismatch analysis (FAMA), and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998)).

The protein truncation test is also useful for detecting the inactivation of a gene in which translation-terminating mutations produce only portions of the encoded protein (see, for example, Stoppa-Lyonnet et al., *Blood* 91:3920 (1998)). According to this approach, RNA is isolated from a biological sample, and used to synthesize cDNA. PCR is then used to amplify the zacrp3×2 target sequence and to introduce an RNA polymerase promoter, a translation initiation sequence, and an in-frame ATG triplet. PCR products are transcribed using an RNA polymerase, and the transcripts are translated in vitro with a T7-coupled reticulocyte lysate system. The translation products are then fractionated by SDS-PAGE to determine the lengths of the translation products. The protein truncation test is described, for example, by Dracopoli et al. (eds.), *Current Protocols in Human Genetics*, pages 9.11.1–9.11.18 (John Wiley & Sons 1998).

The present invention also contemplates kits for performing a diagnostic assay for zacrp3×2 gene expression or to analyze the zacrp3×2 locus of a subject. Such kits comprise nucleic acid probes, such as double-stranded nucleic acid molecules comprising the nucleotide sequence of SEQ ID NO:1, or a fragment thereof, as well as single-stranded nucleic acid molecules having the complement of the nucleotide sequence of SEQ ID NO:1, or a fragment thereof Probe molecules may be DNA, RNA, oligonucleotides, and the like. Kits may comprise nucleic acid primers for performing PCR. Such a kit can contain all the necessary elements to perform a nucleic acid diagnostic assay described above. A kit will comprise at least one container comprising a zacrp3×2 probe or primer. The kit may also comprise a second container comprising one or more reagents capable of indicating the presence of zacrp3×2 sequences. Examples of such indicator reagents include detectable labels such as radioactive labels, fluorochromes, chemiluminescent agents, and the like. A kit may also comprise a means for conveying to the user that the zacrp3×2 probes and primers are used to detect zacrp3×2 gene expression. For example, written instructions may state that the enclosed nucleic acid molecules can be used to detect either a nucleic acid molecule that encodes zacrp3×2, or a nucleic acid molecule having a nucleotide sequence that is complementary to a zacrp3×2-encoding nucleotide sequence, or to analyze chromosomal sequences associated with the zacrp3×2 locus. The written material can be applied directly to a container, or the written material can be provided in the form of a packaging insert.

The present invention also provides reagents which will find use in diagnostic applications. For example, the zacrp3 or zacrp3×2 gene, a probe comprising zacrp3 or zacrp3×2 DNA or RNA or a subsequence thereof can be used to determine if the zacrp3 or zacrp3×2 gene is present on a human chromosome, such as chromosome 5, or if a gene mutation has occurred. Based on annotation of a fragment of human genomic DNA containing a part of zacrp3 or zacrp3×2 genomic DNA (Genbank Accession No. AC010637 and AC010637), zacrp3 or zacrp3×2 is located at the 5p12 region of chromosome 5. Detectable chromosomal aberrations at the zacrp3 or zacrp3×2 gene locus include, but are not limited to, aneuploidy, gene copy number changes, loss of heterozygosity (LOH), translocations, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The zacrp3 or zacrp3×2 gene is located at the 5p12 region of chromosome 5. Several genes of known function map to this region that are linked to human disease. Thus, since the zacrp3 or zacrp3×2 gene maps to chromosome 5p12, the zacrp3 or zacrp3×2 polynucleotide probes of the present invention can be used to detect and diagnose the presence of chromosome 5 monosomy and other chromosome 5p12 loss, and particularly chromosome 5 monosomy and loss and chromosomal aberrations at 5p12 including deletions, rearrangements, and chromosomal breakpoints, and translocations can be associated with tumors. Thus, since the zacrp3 or zacrp3×2 gene maps to this critical region, the zacrp3 or zacrp3×2 polynucleotide probes of the present invention can be used to detect chromosome deletions, translocations and rearrangements associated with those diseases. See the Online Mendellian Inheritance of Man (OMIM™, National Center for Biotechnology Information, National Library of Medicine. Bethesda, Md.) gene map, and references therein, for this region of human chromosome 5, and 5p12 on a publicly available world wide web server. All of these serve as possible candidate genes for an inheritable disease that show linkage to the same chromosomal region as the zacrp3 or zacrp3×2 gene. Thus, zacrp3 or zacrp3×2 polynucleotide probes can be used to detect abnormalities or genotypes associated with these defects.

A diagnostic could assist physicians in determining the type of disease and appropriate associated therapy, or assistance in genetic counseling. As such, the inventive anti-zacrp3 or zacrp3×2 antibodies, polynucleotides, and polypeptides can be used for the detection of zacrp3 or zacrp3×2 polypeptide, mRNA or anti-zacrp3 or zacrp3×2 antibodies, thus serving as markers and be directly used for detecting or genetic diseases or cancers, as described herein, using methods known in the art and described herein.

Further, zacrp3 or zacrp3×2 polynucleotide probes can be used to detect abnormalities or genotypes associated with chromosome 5p12 deletions, chromosome 5 monosomy and translocations associated with human diseases, such as described above, or other translocations and LOH involved with malignant progression of tumors or other 5p12 mutations, which are expected to be involved in chromosome rearrangements in malignancy; or in other cancers. Similarly, zacrp3 or zacrp3×2 polynucleotide probes can be used to detect abnormalities or genotypes associated with chromosome 5p12 trisomy and chromosome loss associated with human diseases or spontaneous abortion. All of these serve as possible candidate genes for an inheritable disease which show linkage to the same chromosomal region as the zacrp3 or zacrp3×2 gene. Thus, zacrp3 or zacrp3×2 polynucleotide probes can be used to detect abnormalities or genotypes associated with these defects.

One of skill in the art would recognize that of zacrp3 or zacrp3×2 polynucleotide probes are particularly useful for diagnosis of gross chromosome 5 abnormalities associated with loss of heterogeneity (LOH), chromosome gain (e.g. trisomy), translocation, chromosome loss (monosomy), DNA amplification, and the like. Translocations within chromosomal locus 5p12 wherein the zacrp3 or zacrp3×2 gene is located are known to be associated with human disease. For example, 5p12 deletions, monosomy and translocations are associated with specific human diseases as discussed above. Thus, since the zacrp3 or zacrp3×2 gene maps to this critical region, zacrp3 or zacrp3×2 polynucleotide probes of the present invention can be used to detect abnormalities or genotypes associated with 5p12 translocation, deletion and trisomy, and the like, described above.

As discussed above, defects in the zacrp3 or zacrp3×2 gene itself may result in a heritable human disease state. Molecules of the present invention, such as the polypeptides, antagonists, agonists, polynucleotides and antibodies of the present invention would aid in the detection, diagnosis prevention, and treatment associated with a zacrp3 or zacrp3×2 genetic defect. In addition, zacrp3 or zacrp3×2 polynucleotide probes can be used to detect allelic differences between diseased or non-diseased individuals at the zacrp3 or zacrp3×2 chromosomal locus. As such, the zacrp3 or zacrp3×2 sequences can be used as diagnostics in forensic DNA profiling.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14–17 nt). PCR primers are at least 5 nt in length, preferably 15 or more, more preferably 20–30 nt. For gross analysis of genes, or chromosomal DNA, a zacrp3 or zacrp3×2 polynucleotide probe may comprise an entire exon or more. Exons are readily determined by one of skill in the art by comparing zacrp3×2 sequences (SEQ ID NO:1) with the genomic DNA for zacrp3 or zacrp3×2 (Genbank Accession No. AC010637 and AC010637). In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a zacrp3 or zacrp3×2 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a zacrp3 or zacrp3×2 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zacrp3 or zacrp3×2 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1 OR SEQ ID NO:5, the complement of SEQ ID NO:1 OR SEQ ID NO:5, or an RNA equivalent thereof. Such methods of showing genetic linkage analysis to human disease phenotypes are well known in the art. For reference to PCR based methods in diagnostics see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the zacrp3 or zacrp3×2 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al.(eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998)). Direct analysis of an zacrp3 or zacrp3×2 gene for a mutation can be performed using a subject's genornic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Use of Anti-Zacrp3x2 Antibodies to Detect Zacrp3x2 Protein

The present invention contemplates the use of anti-zacrp3x2 antibodies to screen biological samples in vitro for the presence of zacrp3x2. In one type of in vitro assay, anti-zacrp3x2 antibodies are used in liquid phase. For example, the presence of zacrp3x2 in a biological sample can be tested by mixing the biological sample with a trace amount of labeled zacrp3x2 and an anti-zacrp3x2 antibody under conditions that promote binding between zacrp3x2 and its antibody. Complexes of zacrp3x2 and anti-zacrp3x2 in the sample can be separated from the reaction mixture by contacting the complex with an immobilized protein which binds with the antibody, such as an Fc antibody or Staphylococcus protein A. The concentration of zacrp3x2 in the biological sample will be inversely proportional to the amount of labeled zacrp3x2 bound to the antibody and directly related to the amount of free labeled zacrp3x2.

Alternatively, in vitro assays can be performed in which anti-zacrp3x2 antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

In another approach, anti-zacrp3x2 antibodies can be used to detect zacrp3x2 in tissue sections prepared from a biopsy specimen. Such immunochemical detection can be used to determine the relative abundance of zacrp3x2 and to determine the distribution of zacrp3x2 in the examined tissue. General immunochemistry techniques are well established (see, for example, Ponder, "Cell Marking Techniques and Their Application," in *Mammalian Development: A Practical Approach*, Monk (ed.), pages 115–38 (IRL Press 1987), Coligan at pages 5.8.1–5.8.8, Ausubel (1995) at pages 14.6.1 to 14.6.13 (Wiley Interscience 1990), and Manson (ed.), *Methods In Molecular Biology, Vol 10: Immunochemical Protocols* (The Humana Press, Inc. 1992)).

Immunochemical detection can be performed by contacting a biological sample with an anti-zacrp3x2 antibody, and then contacting the biological sample with a detectably labeled molecule which binds to the antibody. For example, the detectably labeled molecule can comprise an antibody moiety that binds to anti-zacrp3x2 antibody. Alternatively, the anti-zacrp3x2 antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-zacrp3x2 antibody can be conjugated with a detectable label to form an anti-zacrp3x2 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-zacrp3x2 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhoda-mine, phycoerytherin, phycocyanin, allophycocyanin, o-phthaldehyde and fluorescamine.

Alternatively, anti-zacrp3x2 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-zacrp3x2 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-zacrp3x2 immunoconjugates can be detectably labeled by linking an anti-zacrp3x2 antibody component to an enzyme. When the anti-zacrp3x2-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-zacrp3x2 antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra.

Moreover, the convenience and versatility of immunochemical detection can be enhanced by using anti-zacrp3x2 antibodies that have been conjugated with avidin, streptavidin, and biotin (see, for example, Wilchek et al. (eds.), "Avidin-Biotin Technology," *Methods In Enzymology, Vol.* 184 (Academic Press 1990), and Bayer et al., "Immunochemical Applications of Avidin-Biotin Technology," in *Methods In Molecular Biology, Vol.* 10, Manson (ed.), pages 149–162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180–208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107–120 (Wiley-Liss, Inc. 1995), and Diamandis, *Immunoassay* (Academic Press, Inc. 1996).

In a related approach, biotin- or FITC-labeled zacrp3×2 can be used to identify cells that bind zacrp3×2. Such binding can be detected, for example, using flow cytometry.

The present invention also contemplates kits for performing an immunological diagnostic assay for zacrp3×2 gene expression. Such kits comprise at least one container comprising an anti-zacrp3×2 antibody, or antibody fragment. A kit may also comprise a second container comprising one or more reagents capable of indicating the presence of zacrp3×2 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that zacrp3×2 antibodies or antibody fragments are used to detect zacrp3×2 protein. For example, written instructions may state that the enclosed antibody or antibody fragment can be used to detect zacrp3×2. The written material can be applied directly to a container, or the written material can be provided in the form of a packaging insert.

Use of Zacrp3×2 Polypeptides and Polypeptides

Zacrp3×2 polypeptides, fragments, fusions, agonists or antagonists can be used to modulate energy balance in mammals or to protect endothelial cells from injury. With regard to modulating energy balance, zacrp3×2 polypeptides could find use to modulate cellular metabolic reactions. Such metabolic reactions include adipogenesis, gluconeogenesis, glycogenolysis, lipogenesis, glucose uptake, protein synthesis, thermogenesis, oxygen utilization and the like. Zacrp3×2 may also be evaluated for antimicrobial activity. Zacrp3×2 polypeptide may be used for surgical pretreatment to prevent injury due to ischemia and/or inflammation or in like procedures. Zacrp3×2 polypeptides may also find use as neurotransmitters or as modulators of neurotransmission. In this regard, zacrp3×2 polypeptides may find utility in modulating nutrient uptake, as demonstrated, for example, by 2-deoxy-glucose uptake in the brain or the like.

Among other methods known in the art or described herein, mammalian energy balance may be evaluated by monitoring one or more of the following metabolic functions: adipogenesis, gluconeogenesis, glycogenolysis, lipogenesis, glucose uptake, protein synthesis, thermogenesis, oxygen utilization or the like. These metabolic functions are monitored by techniques (assays or animal models) known to one of ordinary skill in the art, as is more fully set forth below. For example, the glucoregulatory effects of insulin are predominantly exerted in the liver, skeletal muscle and adipose tissue. Insulin binds to its cellular receptor in these three tissues and initiates tissue-specific actions that result in, for example, the inhibition of glucose production and the stimulation of glucose utilization. In the liver, insulin stimulates glucose uptake and inhibits gluconeogenesis and glycogenolysis. In skeletal muscle and adipose tissue, insulin acts to stimulate the uptake, storage and utilization of glucose.

Art-recognized methods exist for monitoring all of the metabolic functions recited above. Thus, one of ordinary skill in the art is able to evaluate zacrp3×2 polypeptides, fragments, fusion proteins, antibodies, agonists and antagonists for metabolic modulating functions. Exemplary modulating techniques are set forth below.

Adipogenesis, gluconeogenesis and glycogenolysis are interrelated components of mammalian energy balance, which may be evaluated by known techniques using, for example, ob/ob mice or db/db mice. The ob/ob mice are inbred mice that are homozygous for an inactivating mutation at the ob (obese) locus. Such ob/ob mice are hyperphagic and hypometabolic, and are believed to be deficient in production of circulating OB protein. The db/db mice are inbred mice that are homozygous for an inactivating mutation at the db (diabetes) locus. The db/db mice display a phenotype similar to that of ob/ob mice, except db/db mice also display a diabetic phenotype. Such db/db mice are believed to be resistant to the effects of circulating OB protein. Also, various in vitro methods of assessing these parameters are known in the art.

Insulin-stimulated lipogenesis, for example, may be monitored by measuring the incorporation of $^{14}$C-acetate into triglyceride (Mackall et al. *J. Biol. Chem.* 251:6462–4, 1976) or triglyceride accumulation (Kletzien et al., *Mol. Pharmacol.* 41:393–8, 1992).

Glucose uptake may be evaluated, for example, in an assay for insulin-stimulated glucose transport. Non-transfected, differentiated L6 myotubes (maintained in the absence of G418) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of insulin or IGF-1, or a dilution series of the test substance, are added, and the cells are incubated for 20–30 minutes. $^{3}$H or $^{14}$C-labeled deoxyglucose is added to ≈50 1M final concentration, and the cells are incubated for approximately 10–30 minutes. The cells are then quickly rinsed with cold buffer (e.g. PBS), then lysed with a suitable lysing agent (e.g. 1% SDS or 1 N NaOH). The cell lysate is then evaluated by counting in a scintillation counter. Cell-associated radioactivity is taken as a measure of glucose transport after subtracting non-specific binding as determined by incubating cells in the presence of cytocholasin b, an inhibitor of glucose transport. Other methods include those described by, for example, Manchester et al., *Am. J. Physiol.* 266 (*Endocrinol. Metab.* 29):E326–E333, 1994 (insulin-stimulated glucose transport).

Protein synthesis may be evaluated, for example, by comparing precipitation of $^{35}$S-methionine-labeled proteins following incubation of the test cells with $^{35}$S-methionine and $^{35}$S-methionine and a putative modulator of protein synthesis.

Thermogenesis may be evaluated as described by B. Stanley in *The Biology of Neuropeptide Y and Related Peptides*, W. Colmers and C. Wahlestedt (eds.), Humana Press, Ottawa, 1993, pp. 457–509; C. Billington et al., *Am. J. Physiol.* 260: R321, 1991; N. Zaujevski et al., *Endocrinology* 133:1753, 1993; C. Billington et al., *Am. J. Physiol.* 266: R1765, 1994; Heller et al., *Am. J. Physiol.* 252(4 Pt 2): R661–7, 1987; and Heller et al., *Am. J. Physiol.* 245: R321–8, 1983. Also, metabolic rate, which may be measured by a variety of techniques, is an indirect measurement of thermogenesis.

Oxygen utilization may be evaluated as described by Heller et al., *Pflugers Arch* 369: 55–9, 1977. This method also involved an analysis of hypothalmic temperature and metabolic heat production. Oxygen utilization and thermoregulation have also been evaluated in humans as described by Haskell et al., *J. Appl. Physiol.* 51: 948–54, 1981.

Among other methods known in the art or described herein, neurotransmission functions may be evaluated by monitoring 2-deoxy-glucose uptake in the brain. This parameter is monitored by techniques (assays or animal models) known to one of ordinary skill in the art, for example, autoradiography. Useful monitoring techniques are described, for example, by Kilduff et al., *J. Neurosci.* 10: 2463–75, 1990, with related techniques used to evaluate the "hibernating heart" as described in Gerber et al. *Circulation* 94: 651–8, 1996, and Fallavollita et al., *Circulation* 95: 1900–9, 1997.

In addition, zacrp3×2 polypeptides, fragments, fusions agonists or antagonists thereof may be therapeutically useful for anti-microbial applications. For example, complement component C1q plays a role in host defense against infectious agents, such as bacteria and viruses. C1q is known to exhibit several specialized functions. For example, C1q triggers the complement cascade via interaction with bound antibody or C-reactive protein (CRP). Also, C1q interacts directly with certain bacteria, RNA viruses, mycoplasma, uric acid crystals, the lipid A component of bacterial endotoxin and membranes of certain intracellular organelles. C1q binding to the C1q receptor is believed to promote phagocytosis. C1q also appears to enhance the antibody formation aspect of the host defense system. See, for example, Johnston, *Pediatr. Infect. Dis. J.* 12(11):933–41, 1993. Thus, soluble C1q-like molecules may be useful as anti-microbial agents, promoting lysis or phagocytosis of infectious agents.

The collagenous domains of proteins such as C1q and macrophage scavenger receptor are know to bind acidic phospholipids such as LPA. The interaction of zacrp3×2 polypeptides, fragments, fusions, agonists or antagonists with mitogenic anions such as LPA can be determined using assays known in the art, see for example, Acton et al., ibid. Inhibition of inflammatory processes by polypeptides and antibodies of the present invention would also be useful in preventing infection at the wound site.

Anti-microbial protective agents may be directly acting or indirectly acting. Such agents operating via membrane association or pore forming mechanisms of action directly attach to the offending microbe. Anti-microbial agents can also act via an enzymatic mechanism, breaking down microbial protective substances or the cell wall/membrane thereof. Anti-microbial agents, capable of inhibiting microorganism proliferation or action or of disrupting microorganism integrity by either mechanism set forth above, are useful in methods for preventing contamination in cell culture by microbes susceptible to that anti-microbial activity. Such techniques involve culturing cells in the presence of an effective amount of said zacrp3×2 polypeptide or an agonist or antagonist thereof.

Also, zacrp3×2 polypeptides or agonists thereof may be used as cell culture reagents in in vitro studies of exogenous microorganism infection, such as bacterial, viral or fungal infection. Such moieties may also be used in in vivo animal models of infection.

Zacrp3×2 fragments as well as zacrp3×2 polypeptides, fusion proteins, agonists, antagonists or antibodies may be evaluated with respect to their anti-microbial properties according to procedures known in the art. See, for example, Barsum et al., *Eur. Respir. J.* 8(5):709–14, 1995; Sandovsky-Losica et al., *J. Med. Vet. Mycol* (England) 28(4):279–87, 1990; Mehentee et al., *J. Gen. Microbiol.* (*England*) 135 (Pt. 8):2181–8, 1989; Segal and Savage, *J. Med. Vet. Mycol.* 24: 477–9, 1986 and the like. If desired, the performance of zacrp3×2 in this regard can be compared to proteins known to be functional in this regard, such as proline-rich proteins, lysozyme, histatins, lactoperoxidase or the like. In addition, zacrp3×2 fragments, polypeptides, fusion proteins, agonists, antagonists or antibodies may be evaluated in combination with one or more anti-microbial agents to identify synergistic effects. One of ordinary skill in the art will recognize that the anti-microbial properties of zacrp3×2 polypeptides, fragments, fusion proteins, agonists, antagonists and antibodies may be similarly evaluated.

As neurotransmitters or neurotransmission modulators, zacrp3×2 polypeptide fragments as well as zacrp3×2 polypeptides, fusion proteins, agonists, antagonists or antibodies of the present invention may also modulate calcium ion concentration, muscle contraction, hormone secretion, DNA synthesis or cell growth, inositol phosphate turnover, arachidonate release, phospholipase-C activation, gastric emptying, human neutrophil activation or ADCC capability, superoxide anion production and the like. Evaluation of these properties can be conducted by known methods, such as those set forth herein.

The impact of zacrp3×2 polypeptide, fragment, fusion, antibody, agonist or antagonist on intracellular calcium level may be assessed by methods known in the art, such as those described by Dobrzanski et al., *Regulatory Peptides* 45: 341–52, 1993, and the like. The impact of zacrp3×2 polypeptide, fragment, fusion, agonist or antagonist on muscle contraction may be assessed by methods known in the art, such as those described by Smits & Lebebvre, *J. Auton. Pharmacol.* 14: 383–92, 1994, Belloli et al., *J. Vet. Pharmacol. Therap.* 17: 379–83, 1994, Maggi et al., *Regulatory Peptides* 53: 259–74, 1994, and the like. The impact of zacrp3×2 polypeptide, fragment, fusion, agonist or antagonist on hormone secretion may be assessed by methods known in the art, such as those for prolactin release described by Henriksen et al., *J. Recep. Sig. Transd. Res.* 15(1–4):529–41, 1995, and the like. The impact of zacrp3×2 polypeptide, fragment, fusion, agonist or antagonist on DNA synthesis or cell growth may be assessed by methods known in the art, such as those described by Dobrzanski et al., *Regulatory Peptides* 45: 341–52, 1993, and the like. The impact of zacrp3×2 polypeptide, fragment, fusion, agonist or antagonist on inositol phosphate turnover may be assessed by methods known in the art, such as those described by Dobrzanski et al., *Regulatory Peptides* 45: 341–52, 1993, and the like.

Also, the impact of zacrp3×2 polypeptide, fragment, fusion, agonist or antagonist on arachidonate release may be assessed by methods known in the art, such as those described by Dobrzanski et al., *Regulatory Peptides* 45: 341–52, 1993, and the like. The impact of zacrp3×2 polypeptide, fragment, fusion, agonist or antagonist on phospholipase-C activation may be assessed by methods known in the art, such as those described by Dobrzanski et al., *Regulatory Peptides* 45: 341–52, 1993, and the like. The impact of zacrp3×2 polypeptide, fragment, fusion, agonist or antagonist on gastric emptying may be assessed by methods known in the art, such as those described by Varga et al., *Eur. J. Pharmacol.* 286: 109–112, 1995, and the like. The impact of zacrp3×2 polypeptide, fragment, fusion, agonist or antagonist on human neutrophil activation and ADCC capability may be assessed by methods known in the art, such as those described by Wozniak et al., *Immunology* 78: 629–34, 1993, and the like. The impact of zacrp3×2 polypeptide, fragment, fusion, agonist or antagonist on superoxide anion production may be assessed by methods known in the art, such as those described by Wozniak et al., *Immunology* 78: 629–34, 1993, and the like.

The effect of zacrp3×2 on expression of cell surface adhesion molecules such as E-selectin (endothelial leukocyte adhesion molecule), V-CAM (vascular cell adhesion molecule), and I-CAM (intercellular adhesion molecule) can be measured using microvascular bone marrow cells (TRBMEC) in a cell ELISA according to Ouchi et al., (*Circulation* 100:2473–7, 1999). This activity can be compared to the stimulation from inflammatory cytokines such as TNF (tumor necrosis factor). A THP-1 monocyte adherence assay according to Ouchi et al., (ibid.) and Cybulsky and Gimbrone, (*Science* 251:788–91, 1991) may be used to measure zacrp3×2 activity as well.

Collagen is a potent inducer of platelet aggregation. Platelets interact with damaged vessel walls to form a thrombus. The degree of response is graded due to the subendothelium tissue exposed and the blood flow in the injured area. This poses risks to patients recovering from vascular injuries. Inhibitors of collagen-induced platelet aggregation would be useful for blocking the binding of platelets to collagen-coated surfaces and reducing associated collagen-induced platelet aggregation. C1q is a component of the complement pathway and has been found to stimulate defense mechanisms as well as trigger the generation of toxic oxygen species that can cause tissue damage (Tenner, *Behring Inst. Mitt.* 93:241–53, 1993). C1q binding sites are found on platelets. C1q, independent of an immune binding partner, has been found to inhibit platelet aggregation but not platelet adhesion or shape change. The amino terminal region of C1q shares homology with collagen (Peerschke and Ghebrehiwet, *J. Immunol.* 145:2984–88, 1990). Inhibition of C1q and the complement pathway can be determined using methods disclosed herein or know in the art, such as described in Suba and Csako, *J. Immunol.* 117:304–9, 1976. In this regard, zacrp3×2 polypeptides would be useful in modulating hemostasis, increasing blood flow flowing vascular injury and pacifying collagenous surfaces.

The activity of zacrp3×2 polypeptide, fragments, fusions, agonists or antagonists on collagen-mediated platelet adhesion, activation and aggregation may be measured using methods described herein or known in the art, such as the platelet aggregation assay (Chiang et al., *Thrombosis Res.* 37:605–12, 1985) and platelet adhesion assays (Peerschke and Ghebrehiwet, *J. Immunol.* 144:221–25, 1990). Assays for platelet adhesion to collagen and inhibition of collagen-induced platelet aggregation can be measured using methods described in Keller et al., *J. Biol. Chem.* 268:5450–6, 1993; Waxman and Connolly, *J. Biol. Chem.* 268:5445–9, 1993; Noeske-Jungblut et al., *J. Biol. Chem.* 269:5050–3 or 1994 Deckinyn et al., *Blood* 85:712–9, 1995.

Zacrp3×2 polypeptides, fragments, fusion proteins, antibodies, agonists or antagonists of the present invention can be used in methods for promoting blood flow within the vasculature of a mammal by reducing the number of platelets that adhere and are activated and the size of platelet aggregates. Such methods would comprise administration of a therapeutically effective amount of zacrp3×2 polypeptides, fragments, fusions, antibodies, agonists or antagonists to a mammal in need of such treatment, whereby zacrp3×2 reduces thrombogenic and complement activity within the vasculature of the mammal. Zacrp3×2 polypeptides, fragments, fusions, antibodies, agonists or antagonists used in such methods can be administered prior to, during or following an acute vascular injury in the mammal.

In one such method, the vascular injury is due to vascular reconstruction, including but not limited to, angioplasty, endarterectomy, coronary artery bypass graft, microvascular repair or anastomosis of a vascular graft. Also contemplated are vascular injuries due to trauma, stroke or aneurysm. In other preferred methods the vascular injury is due to plaque rupture, degradation of the vasculature, complications associated with diabetes and atherosclerosis. Plaque rupture in the coronary artery induces heart attack and in the cerebral artery induces stroke. Use of zacrp3×2 polypeptides, fragments, fusion proteins, antibodies, agonists or antagonists in such methods would also be useful for ameliorating whole system diseases of the vasculature associated with the immune system, such as disseminated intravascular coagulation (DIC) and SIDs. Additionally the complement inhibiting activity would be useful for treating non-vasculature immune diseases such as arteriolosclerosis.

A correlation has been found between the presence of C1q in localized ischemic myocardium and the accumulation of leukocytes following coronary occlusion and reperfusion. Release of cellular components following tissue damage triggers complement activation which results in toxic oxygen products that may be the primary cause of myocardial damage (Rossen et al., *Circ. Res.* 62:572–84, 1998 and Tenner, ibid.). Blocking the complement pathway was found to protect ischemic myocardium from reperfusion injury (Buerke et al., *J. Pharm. Exp. Therp.* 286:429–38, 1998). The complement inhibition and C1q binding activity of zacrp3×2 polypeptides would be useful for such purposes.

The activity of zacrp3×2 polypeptide, fragments, fusions, agonists or antagonists on vasodilation of aortic rings can be measured according to the methods of Dainty et al., *J. Pharmacol.* 100:767, 1990 and Rhee et al., *Neurotox.* 16:179, 1995.

Various in vitro and in vivo models are available for measuring the effect of zacrp3×2 polypeptides, fragments, fusion proteins, antibodies, agonists and antagonists on ischemia and reperfusion injury. See for example, Shandelya et al., *Circulation* 88:2812–26, 1993; Weisman et al., *Science* 249:146–151, 1991; Buerke et al., *Circulation* 91:393–402, 1995; Horstick et al., *Circulation* 95:701–8, 1997 and Burke et al., *J. Phar. Exp. Therp.* 286:429–38, 1998. An ex vivo hamster platelet aggregation assay is described by Deckmyn et al., ibid. Bleeding times in hamsters and baboons can be measured following injection of zacrp3×2 polypeptides using the model described by Deckmyn et al., ibid. The formation of thrombus in response to administration of proteins of the present invention can be measured using the hamster femoral vein thrombosis model is provided by Deckmyn et al., ibid. Changes in platelet adhesion under flow conditions following administration of zacrp3×2 can be measured using the method described in Harsfalvi et al., *Blood* 85:705–11, 1995.

Complement inhibition and wound healing activity of zacrp3×2 polypeptides, fragments, fusion proteins, antibodies, agonists or antagonists can be assayed alone or in combination with other know inhibitors of collagen-induced platelet activation and aggregation, such as palldipin, moubatin or calin, for example.

Zacrp3×2 polypeptides, fragments, fusion proteins, antibodies, agonists or antagonists can be evaluated using methods described herein or known in the art, such as healing of dermal layers in pigs (Lynch et al., *Proc. Natl. Acad. Sci. USA* 84: 7696–700, 1987) and full-thickness skin wounds in genetically diabetic mice (Greenhalgh et al., *Am. J. Pathol.* 136: 1235–46, 1990), for example. The polypeptides of the present invention can be assayed alone or in combination with other known complement inhibitors as described above.

Proteins that bind collagen are useful to pacify damaged collagenous tissues preventing platelet adhesion, activation or aggregation, and the activation of inflammatory processes which lead to the release of toxic oxygen products. By rendering the exposed tissue inert towards such processes as complement activity, thrombotic activity and immune activation, zacrp3×2 polypeptides, fragments, fusions, antibodies, agonists or antagonists would be useful in reducing the injurious effects of ischemia and reperfusion. In particular, such injuries would include trauma injury ischemia, intestinal strangulation, and injury associated with pre- and post-establishment of blood flow. Zacrp3×2 would be useful in the treatment of cardiopulmonary bypass ischemia and recesitation, myocardial infarction and post trauma vasospasm, such as stroke or percutanious transluminal angioplasty as well as accidental or surgical-induced vascular trauma.

Zacrp3×2 polypeptides, fragments, fusions, antibodies, agonists or antagonists would also be useful to pacify prosthetic biomaterials and surgical equipment to render the surface of the materials inert towards complement activation, thrombotic activity or immune activation. Such materials include, but are not limited to, collagen or collagen fragment-coated biomaterials, gelatin-coated biomaterials, fibrin-coated biomaterials, fibronectin-coated biomaterials, heparin-coated biomaterials, collagen and gel-coated stents, arterial grafts, synthetic heart valves, artificial organs or any prosthetic application exposed to blood that will bind zacrp3×2 at greater than $1 \times 10^8$. Coating such materials can be done using methods known in the art, see for example, Rubens, U.S. Pat. No. 5,272,074.

Complement and Clq play a role in inflammation. The complement activation is initiated by binding of Clq to immunoglobulins (Johnston, *Pediatr. Infect. Dis. J.* 12:933–41, 1993; Ward and Ghetie, *Therap. Immunol.* 2:77–94, 1995). Inhibitors of Clq and complement would be useful as anti-inflammatory agents. Such application can be made to prevent infection. Additionally, such inhibitors can be administrated to an individual suffering from inflammation mediated by complement activation and binding of immune complexes to Clq. Zacrp3×2 polypeptides, fragments, fusion proteins, antibodies, agonists or antagonists would be useful in methods of mediating wound repair, enhancing progression in wound healing by overcoming impaired wound healing. Progression in wound healing would include, for example, such elements as a reduction in inflammation, fibroblasts recruitment, wound retraction and reduction in infection.

Ability of tumor cells to bind to collagen may contribute to the metastasis of tumors. Inhibitors of collagen binding are also useful for mediating the adhesive interactions and metastatic spread of tumors (Noeske-Jungbult et al., U.S. Pat. No. 5,723,312).

Platelet adhesion, activation and aggregation can be evaluated using methods described herein or known in the art, such as the platelet aggregation assay (Chiang et al., *Thrombosis Res.* 37:605–12, 1985) and platelet adhesion assays (Peerschke and Ghebrehiwet, *J. Immunol.* 144:221–25, 1990) Inhibition of Clq and the complement pathway can be determined using methods disclosed herein or know in the art, such as described in Suba and Csako, *J. Immunol.* 117:304–9, 1976. Assays for platelet adhesion to collagen and inhibition of collagen-induced platelet aggregation can be measured using methods described in Keller et al., *J. Biol. Chem.* 268:5450–6, 1993; Waxman and Connolly, *J. Biol. Chem.* 268:5445–9, 1993; Noeske-Jungblut et al., *J. Biol. Chem.* 269:5050–3 or 1994 Deckmyn et al., *Blood* 85:712–9, 1995.

The positively charged, extracellular, triple helix, collagenous domains of Clq and macrophage scavenger receptor were determined to play a role in ligand binding and were shown to have a broad binding specificity for polyanions (Acton et al., *J. Biol. Chem.* 268:3530–37, 1993). Lysophospholipid growth factor (lysophatidic acid, LPA) and other mitogenic anions localize at the site of damaged tissues and assist in wound repair. LPA exerts many biological effects including activation of platelets and up-regulation of matrix assembly. It is thought that LPA synergizes with other blood coagulation factors and mediates wound healing.

Therapeutic Uses of Polypeptides having Zacrp3×2 Activity

The present invention includes the use of proteins, polypeptides, and peptides having zacrp3×2 activity (such as zacrp3×2 polypeptides, anti-idiotype anti-zacrp3×2 antibodies, and zacrp3×2 fusion proteins) to a subject in need of a zacrp3×2 protein.

Generally, the dosage of administered polypeptide, protein or peptide will vary depending upon such factors as the patient's age, weight, height, sex, general medical condition and previous medical history. Typically, it is desirable to provide the recipient with a dosage of a molecule having zacrp3×2 activity which is in the range of from about 1 pg/kg to 10 mg/kg (amount of agent/body weight of patient), although a lower or higher dosage also may be administered as circumstances dictate.

Administration of a molecule having zacrp3×2 activity to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses. One form of administration is made at or near the site of vascular injury.

A pharmaceutical composition comprising a protein, polypeptide, or peptide having zacrp3×2 activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, molecules having zacrp3×2 activity and a pharmaceutically acceptable carrier are administered to a patient in a therapeutically effective amount. A combination of a protein, polypeptide, or peptide having zacrp3×2 activity and a pharmaceutically acceptable carrier is said to be administered in a "therapeutically effective amount" if the amount administered is physiologically significant. An agent is physiologically significant if its presence results in a detectable change in the physiology of a recipient patient as noted by the clinician or other qualified observer.

A pharmaceutical composition comprising molecules having zacrp3×2 activity can be furnished in liquid form, or in solid form. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, *Pharmaceutical Dosage Forms and Drug Delivery Systems*, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

As an illustration, zacrp3×2 pharmaceutical compositions may be supplied as a kit comprising a container that comprises zacrp3x2. zacrp3x2 can be provided in the form of an injectable solution for single or multiple doses, or as a sterile powder that will be reconstituted before injection. Such a kit may further comprise written information on indications and usage of the pharmaceutical composition. Moreover, such information may include a statement that the zacrp3x2 composition is contraindicated in patients with known hypersensitivity to zacrp3x2.

Educational Uses

Polynucleotides and polypeptides of the present invention will be useful as educational tools in laboratory practicum kits for courses related to genetics and molecular biology, protein chemistry, and antibody production and analysis. Due to its unique polynucleotide and polypeptide sequences, molecules of zacrp3x2 can be used as standards or as "unknowns" for testing purposes. For example, zacrp3x2 polynucleotides can be used as an aid, such as, for example, to teach a student how to prepare expression constructs for bacterial, viral, or mammalian expression, including fusion constructs, wherein zacrp3x2 is the gene to be expressed; for determining the restriction endonuclease cleavage sites of the polynucleotides; determining mRNA and DNA localization of zacrp3x2 polynucleotides in tissues (i.e., by northern and Southern blotting as well as polymerase chain reaction); and for identifying related polynucleotides and polypeptides by nucleic acid hybridization.

Zacrp3x2 polypeptides can be used as an aid to teach preparation of antibodies; identifying proteins by western blotting; protein purification; determining the weight of produced zacrp3x2 polypeptides as a ratio to total protein produced; identifying peptide cleavage sites; coupling amino and carboxyl terminal tags; amino acid sequence analysis, as well as, but not limited to monitoring biological activities of both the native and tagged protein in vitro and in vivo.

Zacrp3x2 polypeptides can also be used to teach analytical skills such as mass spectrometry, circular dichroism to determine conformation, especially of the four alpha helices, x-ray crystallography to determine the three-dimensional structure in atomic detail, nuclear magnetic resonance spectroscopy to reveal the structure of proteins in solution. For example, a kit containing the zacrp3x2 can be given to the student to analyze. Since the amino acid sequence would be known by the instructor, the protein can be given to the student as a test to determine the skills or develop the skills of the student, the instructor would then know whether or not the student has correctly analyzed the polypeptide. Since every polypeptide is unique, the educational utility of zacrp3×2 would be unique unto itself.

The antibodies which bind specifically to zacrp3×2 can be used as a teaching aid to instruct students how to prepare affinity chromatography columns to purify zacrp3×2, cloning and sequencing the polynucleotide that encodes an antibody and thus as a practicum for teaching a student how to design humanized antibodies. The zacrp3×2 gene, polypeptide, or antibody would then be packaged by reagent companies and sold to educational institutions so that the students gain skill in art of molecular biology. Because each gene and protein is unique, each gene and protein creates unique challenges and learning experiences for students in a lab practicum. Such educational kits containing the zacrp3×2 gene, polypeptide, or antibody are considered within the scope of the present invention.

Therapeutic Uses of Zacrp3×2 Nucleotide Sequences

The present invention includes the use of zacrp3×2 nucleotide sequences to provide zacrp3×2 to a subject in need of such treatment. In addition, a therapeutic expression vector can be provided that inhibits zacrp3×2 gene expression, such as an anti-sense molecule, a ribozyme, or an external guide sequence molecule.

There are numerous approaches to introduce a zacrp3×2 gene to a subject, including the use of recombinant host cells that express zacrp3×2, delivery of naked nucleic acid encoding zacrp3×2, use of a cationic lipid carrier with a nucleic acid molecule that encodes zacrp3×2, and the use of viruses that express zacrp3×2, such as recombinant retroviruses, recombinant adeno-associated viruses, recombinant adenoviruses, and recombinant Herpes simplex viruses (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)). In an ex vivo approach, for example, cells are isolated from a subject, transfected with a vector that expresses a zacrp3×2 gene, and then transplanted into the subject.

In order to effect expression of a zacrp3×2 gene, an expression vector is constructed in which a nucleotide sequence encoding a zacrp3×2 gene is operably linked to a core promoter, and optionally a regulatory element, to control gene transcription. The general requirements of an expression vector are described above.

Alternatively, a zacrp3×2 gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.* 193:653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad. Sci. USA* 86:317 (1989), and Flexner et al., *Ann. N.Y. Acad. Sci.* 569:86 (1989)), and retroviruses (e.g., Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399,346). Within various embodiments, either the viral vector itself, or a viral particle which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant HSV can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), *HSV Virus Protocols* (Humana Press 1997).

Alternatively, an expression vector comprising a zacrp3×2 gene can be introduced into a subject's cells by lipofection in vivo using liposomes. Synthetic cationic lipids can be used to prepare liposomes for in vivo transfection of a gene encoding a marker (Felgner et al., *Proc. Nat'l Acad. Sci. USA* 84:7413 (1987); Mackey et al., *Proc. Nat'l Acad. Sci. USA* 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Electroporation is another alternative mode of administration of a zacrp3×2 nucleic acid molecules. For example, Aihara and Miyazaki, *Nature Biotechnology* 16:867 (1998), have demonstrated the use of in vivo electroporation for gene transfer into muscle.

In an alternative approach to gene therapy, a therapeutic gene may encode a zacrp3×2 anti-sense RNA that inhibits the expression of zacrp3×2. Methods of preparing anti-sense constructs are known to those in the art. See, for example, Erickson et al., *Dev. Genet.* 14:274 (1993) [transgenic mice], Augustine et al., *Dev. Genet.* 14:500 (1993) [murine whole embryo culture], and Olson and Gibo, *Exp. Cell Res.* 241:134 (1998) [cultured cells]. Suitable sequences for zacrp3×2 anti-sense molecules can be derived from the nucleotide sequences of zacrp3×2 disclosed herein.

Alternatively, an expression vector can be constructed in which a regulatory element is operably linked to a nucleotide sequence that encodes a ribozyme. Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). In the context of the present invention, ribozymes include nucleotide sequences that bind with zacrp3×2 mRNA.

In another approach, expression vectors can be constructed in which a regulatory element directs the production of RNA transcripts capable of promoting RNase P-mediated cleavage of mRNA molecules that encode a zacrp3×2 gene. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053, Yuan et al., *Science* 263:1269 (1994), Pace et al., international publication No. WO 96/18733, George et al., international publication No. WO 96/21731, and Werner et al., international publication No. WO 97/33991). Preferably, the external guide sequence comprises a ten to fifteen nucleotide sequence complementary to zacrp3×2 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having a zacrp3×2 nucleotide acid sequence, such as a recombinant virus, will vary depending upon such factors as the subjects age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, *Remington's Pharmaceutical Sciences, 19th Ed.* (Mack Publishing Co. 1995), and *Gilman's the Pharmacological Basis of Therapeutics, 7th Ed.* (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

Production of Transgenic Mice

Transgenic mice can be engineered to over-express the zacrp3×2 gene in all tissues or under the control of a tissue-specific or tissue-preferred regulatory element. These over-producers of zacrp3×2 can be used to characterize the phenotype that results from over-expression, and the transgenic animals can serve as models for human disease caused by excess zacrp3×2. Transgenic mice that over-express zacrp3×2 also provide model bioreactors for production of zacrp3×2 in the milk or blood of larger animals. Methods for producing transgenic mice are well-known to those of skill in the art (see, for example, Jacob, "Expression and Knockout of Interferons in Transgenic Mice," in *Overexpression and Knockout of Cytokines in Transgenic Mice*, Jacob (ed.), pages 111–124 (Academic Press, Ltd. 1994), Monastersky and Robl (eds.), *Strategies in Transgenic Animal Science* (ASM Press 1995), and Abbud and Nilson, "Recombinant Protein Expression in Transgenic Mice," in *Gene Expression Systems: Using Nature for the Art of Expression*, Fernandez and Hoeffler (eds.), pages 367–397 (Academic Press, Inc. 1999)).

For example, a method for producing a transgenic mouse that expresses a zacrp3×2 gene can begin with adult, fertile males (studs) (B6C3f1, 2–8 months of age (Taconic Farms, Germantown, N.Y.)), vasectomized males (duds) (B6D2f1, 2–8 months, (Taconic Farms)), prepubescent fertile females (donors) (B6C3f1, 4–5 weeks, (Taconic Farms)) and adult fertile females (recipients) (B6D2f1, 2–4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46–47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, *Biol. Reprod.* 77:159 (1986), and Dienhart and Downs, *Zygote* 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a zacrp3×2 encoding sequence is linearized, gel-purified, and resuspended in 10 mM Tris-HCl (pH 7.4), 0.25 mM EDTA (pH 8.0), at a final concentration of 5–10 nanograms per microliter for microinjection. For example, the zacrp3×2 encoding sequences can encode the amino acid residues of SEQ ID NO:2.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12–17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19–21 days gestation. After birth, 19–21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a zacrp3×2 gene or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5–2 cm incision is made below the sternum and the left lateral lobe of the liver exteriorized. Using 4–0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7–10 days after surgery. The expression level of zacrp3×2 mRNA is examined for each transgenic mouse using an RNA solution hybridization assay or polymerase chain reaction.

In addition to producing transgenic mice that over-express zacrp3×2, it is useful to engineer transgenic mice with either abnormally low or no expression of the gene. Such transgenic mice provide useful models for diseases associated with a lack of zacrp3×2. As discussed above, zacrp3×2 gene expression can be inhibited using anti-sense genes, ribozyme genes, or external guide sequence genes. To produce transgenic mice that under-express the zacrp3×2 gene, such inhibitory sequences are targeted to zacrp3×2 mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in *Methods in Gene Biotechnology*, pages 205–224 (CRC Press 1997)).

An alternative approach to producing transgenic mice that have little or no zacrp3×2 gene expression is to generate mice having at least one normal zacrp3×2 allele replaced by a nonfunctional zacrp3×2 gene. One method of designing a nonfunctional zacrp3×2 gene is to insert another gene, such as a selectable marker gene, within a nucleic acid molecule that encodes zacrp3×2. Standard methods for producing these so-called "knockout mice" are known to those skilled in the art (see, for example, Jacob, "Expression and Knockout of Interferons in Transgenic Mice," in *Overexpression and Knockout of Cytokines in Transgenic Mice*, Jacob (ed.), pages 111–124 (Academic Press, Ltd. 1994), and Wu et al., "New Strategies for Gene Knockout," in *Methods in Gene Biotechnology*, pages 339–365 (CRC Press 1997)).

The invention is further illustrated by the following non-limiting example.

EXAMPLES

Example 1
Tissue Distribution of Human Zacrp3×2 in Tissue Panels Using PCR

A panel of cDNAs from human tissues was screened for human zacrp3 (Piddington et al., WO 00/63377) expression using PCR. The panel was made in-house and contained marathon cDNA and cDNA samples from various normal and cancerous human tissues and cell lines and is shown in Table 4, below. The cDNAs came from in-house libraries or marathon cDNAs from in-house RNA preps, Clontech RNA, or Invitrogen RNA. The marathon cDNAs were made using the marathon-Ready™ kit (Clontech, Palo Alto, Calif.) and QC tested with clathlrin primers ZC21,195 (SEQ ID NO:9) and ZC21,196 (SEQ ID NO:10) and then diluted based on the intensity of the clathrin band. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo ZC14,063 (SEQ ID NO:11) and 3' alpha tubulin specific oligo primer ZC17,574 (SEQ ID NO:12) or 3' G3PDH specific oligo primer ZC17,600 (SEQ ID NO:13) and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2–100 pg/µl of cDNA. The PCR reactions for human zacrp3 were set up using oligos ZC23,989 (SEQ ID NO:14) and ZC23,899 (SEQ ID NO:15). The amplification was carried out as follows:1 cycle at 94° C. for 2 minutes, 35 cycles of 94° C. for 15 seconds, 68° C. for 45 seconds, followed by 1 cycle at 72° C. for 7 minutes. About 10 µl of the PCR reaction product was subjected to agarose gel electrophoresis using a 4% agarose gel. In addition to the expected zacrp3 band at 229 bp was a band of approximately 600 bp.

The PCR products from brain, fetal liver, kidney, prostate, spinal cord, and salivary gland were excised, pooled, and purified using Qiaex II (Qiagen, Chatsworth, Calif.) according to manufacturer's instructions and submitted for sequence analysis. Sequencing identified the 600 bp band as a splice variant of zacrp3. A 73 amino acid residue splice occurs 7 amino acids residues following the start Met of zacrp3. Zacrp3 and zacrp3×2 are differentially expressed, see Table 4 below (bold entries signify expression by both zacrp3 and zacrp3×2, X signifies expression by zacrp3×2 alone). Zacrp3×2 independently expressed in brain, lymph node, mammary gland, placenta, uterus, and fetal liver.

TABLE 4

| Tissue/Cell line/ Library | # samples | Tissue/Cell line/ Library | # samples |
| --- | --- | --- | --- |
| Adrenal gland | 1 | Stomach Tumor | 1 |
| Bladder | 1 | WI38 | 1 |
| Bone Marrow | 2 | Islet | 1 |
| Brain X | 1 | Arrayed Bone Marrow | 1 |
| Cervix | 1 | RPMI #1788 (ATCC # CCL-156) | 1 |
| Colon | 1 | Arrayed Fetal Brain | 1 |
| Fetal brain | 2 | Arrayed Heart | 1 |
| Fetal heart | 2 | Adipocyte | 1 |
| Fetal kidney | 1 | MG63 | 1 |
| Fetal liver | 2 | HaCat - human keratinocytes | 1 |
| Fetal lung | 1 | HPV (ATCC # CRL-2221) | 1 |
| Fetal muscle | 1 | Arrayed Pituitary | 1 |
| Fetal skin | 1 | Prostate SM | 1 |
| Heart | 2 | CD3+ selected PBMC's Ionomycin + PMA stimulated | 1 |
| K562 (ATCC # CCL-243) | 1 | HPVS (ATCC # CRL-2221) - selected | 1 |
| Kidney | 2 | Arrayed Placenta HP1C | 1 |
| Liver | 1 | Arrayed Placenta HP2C X | 1 |
| Lung | 1 | Arrayed Salivary | 1 |
| Lymph node X | 1 | Arrayed Testis 1K | 1 |
| Melanoma | 1 | Arrayed Testis 10K | 1 |
| Pancreas | 1 | Prostate 0.5–1.6 kb | 1 |
| Pituitary | 1 | Prostate >1.6 kb | 1 |
| Placenta | 1 | | |
| Prostate | 1 | | |
| Rectum | 1 | | |
| Salivary Gland | 1 | | |
| Skeletal muscle | 1 | | |
| Small intestine | 1 | | |
| Spinal cord | 2 | | |
| Spleen | 1 | | |
| Stomach | 1 | | |
| Testis | 3 | | |
| Thymus | 1 | | |
| Thyroid | 2 | | |
| Trachea | 1 | | |
| Uterus X | 1 | | |
| Esophagus tumor | 1 | | |
| Mammary gland X | 1 | | |
| Ovary | 1 | | |

TABLE 4-continued

| Tissue/Cell line/ Library | # samples | Tissue/Cell line/ Library | # samples |
| --- | --- | --- | --- |
| Liver tumor | 1 | | |
| Lung tumor | 1 | | |
| Ovarian tumor | 1 | | |
| Rectal tumor | 1 | | |
| Uterus tumor | 2 | | |

B. RT PCR Experiment for zacrp3 from Normal vs. Diseased Heart

A RT PCR experiment was done for zacrp3. The RT PCR contained 9 RNA samples from fetal, normal or diseased heart. Samples were purchased or from in-house sources and included fetal heart at 6 weeks, 9 weeks, and 12 weeks; Diseased heart (right and left ventricles), and normal heart. RT PCR reactions were set up using oligos ZC23898 (SEQ ID NO:16) and ZC23899 (SEQ ID NO:17). An annealing temp of 64.6 degrees with an extension time of 30 seconds and a total of 35 cycles were run Superscript One step RT_PCR System (GibCo-BRL). Positive samples for zacrp3×2 were fetal heart at 6, 9 and 12 weeks. Positive samples for zacrp3×1 (WIPO publication WO00/63377) were fetal heart at 6, 9 and 12 weeks, normal heart and diseased heart both right and left ventricle samples.

Example 2

Cloning and Isolation of Zacrp3×2

A. To Obtain a Tangible Full-length cDNA for Zacrp3×2 the Following PCR Reaction was Set-up A PCR reaction using oligos ZC38824 (SEQ ID NO:18) and ZC38825 (SEQ ID NO:19), annealing temp of 62 degrees, 35 cycles and TaKaRa ExTaq (TaKaRa biomedicals, Japan) was run to obtain a ~1.036 kb fragment from human heart cDNA. The product was purified using the QIAquick gel extraction kit (Qiagen, Santa Clarita, Calif.). The 1.036 kb fragment was then ligated into the vector pCR4.0-TOPO using the TOPO TA Cloning Kit for sequencing (Invitrogen, Carlsbad, Calif.).

Clones were screened by PCR using oligos ZC21909 (SEQ ID NO:20) and ZC20838 (SEQ ID NO:21), annealing temp of 55 degrees, 35 cycles and TaKaRa ExTaq (TaKaRa biomedicals, Japan) was run to obtain a ~131 bp fragment. Two clones were sent to sequencing. Base pair differences in clones than from expected.

Digestion of two clones with EcoRI (GibCo-BRL) and SmaI (GibCo-BRL) generated fragments that were ligated together to obtain a correct tangible full-length cDNA for zacrp3×2 as shown in SEQ ID NO:1, encoding the polypeptide sequence of zacrp3×2 as shown in SEQ ID NO:2.

Example 3

Chromosomal Assignment and Placement of Zacrp3

Zacrp3 was mapped to human chromosome 5 using the commercially available version of the Stanford G3 Radiation Hybrid Mapping Panel (Research Genetics, Inc., Huntsville, Ala.). The Stanford G3 RH Panel contains PCRable DNAs from each of 83 radiation hybrid clones of the whole human genome, plus two control DNAs (the RM donor and the A3 recipient). A publicly available WWW server (http:H/shgc-www.stanford.edu) allows chromosomal localization of markers.

For the mapping of zacrp3 with the Stanford G3 RH Panel, 20 µl reactions were set up in a 96-well microtiter plate (Stratagene, La Jolla, Calif.) and used in a RoboCycler Gradient 96 thermal cycler (Stratagene). Each of the 85 PCR reactions consisted of 2 µl 10× KlenTaq PCR reaction buffer (Clontech Laboratories, Inc., Palo Alto, Calif.), 1.6 µl dNTPs mix (2.5 mM each, PERKIN-ELMER, Foster City, Calif.), 1 µl sense primer, ZC 21,913 (SEQ ID NO:22), 1 µl antisense primer, ZC 21,914 (SEQ ID NO:23), 2 µl Redi-Load (Research Genetics, Inc.), 0.4 µl 50× Advantage Klen-Taq Polymerase Mix (Clontech Laboratories, Inc.), 25 ng of DNA from an individual hybrid clone or control and ddH$_2$O for a total volume of 20 µl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 62° C. and 1 minute and 15 seconds extension at 72° C., followed by a final 1 cycle extension of 7 minutes at 72° C. The reactions were separated by electrophoresis on a 2% agarose gel (Life Technologies, Gaithersburg, Md.).

The results showed linkage of Zacrp3 to the human chromosome 5 framework marker SHGC-56588 with a LOD score of 15.58 and at a distance of 0 cR_10000 from the marker. The use of surrounding markers positions Zacrp3 in the 5p12 region on the integrated LDB human chromosome 5 map (The Genetic Location Database, University of Southhampton, WWW server: http://cedar.genetics.soton.ac.uk/public_html/).

Genomic clones also show the chromosomal localization of zacrp3, and its variant zacrp3×2 at 5p12–p13.3 (Genbank Accession No.'s AC010637 and AC010637).

Example 4

Adhesion Molecule Assays

Upon stimulation with inflammatory cytokines such as TNF (tumor necrosis factor), human microvascular bone marrow cells (TRBMEC) express cell surface adhesion molecules, including E-selectin (endothelial leukocyte adhesion molecule), V-CAM (vascular cell adhesion molecule), and I-CAM (intercellular adhesion molecule.

The effect of zacrp3×2 on expression of cell surface adhesion molecules is determined using microvascular bone marrow cells (TRBMEC) in a cell based ELISA according to Ouchi et al., (*Circulation* 100:2473–7, 1999). Briefly, TRBMEC cells are grown in 96 well, flat bottom plates (Costar, Pleasanton, Calif.) until confluent. Both wild type control media and zacrp3×2 media from cells expressing zacrp3×2 is concentrated 10× before testing (Centricon Centrifugal Filtration Unit 5,000K cutoff, Millipore Corp., Bedford, Mass.) according to the manufacturer's instructions. To each well 90 µl of zacrp3×2-containing media or control media is added, and the plates are incubated at 37° C., 5% CO$_2$ overnight. The next day, half of the samples received 10 µl of TNF (10 ng/ml, R&D Systems, Minneapolis, Minn.), the other samples are untreated, measuring basal expression. The plates are then incubated at 37° C., 5% CO$_2$ for 4 hours.

Following incubation, the media is removed from the plates and 50 µl anti-human VCAM antibody (1:1000 dilution of a 1 mg/ml stock, R&D Systems), 50 µl of anti-human ICAM-1 monoclonal antibody (1:1000 dilution of a 1 mg/ml stock, R&D Systems), or 50 µl of anti-human E-selectin antibodies (1:1000 dilution of a 1 mg/ml stock, R&D Systems) are then added to triplicate wells and the plates are incubated at 37° C., 5% CO$_2$ for 1 hour.

The antibody solution is removed and the plates are washed three times in warm RPMI+5% FBS. Following the last wash, 100 μl/well of an 0.05% gluteraldehyde solution (1:1000 of 50% gluteraldehyde in PBS) is added to the wells and the plates are incubated at room temperature for 10 minutes. The plates are washed three times with PBS and 50 μl/well of secondary antibody (1:1000 dilution of goat anti-mouse IgG whole molecule HRP conjugate, (Sigma Chemical Co., St. Louis, Mo.) is added to all wells. The plates are incubated for one hour at 37° C.

The plates are then washed five times with washing buffer (PBS+0.05% Tween 20) and 100 μl/well TMB solution (100 μl of 4 mg/ml Tetra methyl benzidine (Sigma) in DMSO, in 10 ml 60 mM Na Acetate pH 5.0 and 100 μl 1.2% $H_2O_2$) is added to each well. The plates are allowed to develop at room temperature for 15–20 minutes at which time the reaction is quenched by adding 100 μl/well 1M $H_2SO_4$. Plates are read at 450 nm with reference wavelength of 655 nm.

Like zacrp3 (SEQ ID NO:3), zacrp3×2 is expected to show no effect on ICAM-1 expression, but to show an effect on VCAM-1 expression. When compared to the maximal TNF response, zacrp3 treated cells showed about 50% inhibition. Zacrp3 also had an effect, although less, 10% inhibition of E-selection expression. Zacrp3×2 is also expected to show similar activity.

VCAM-1 expression is measured following direct adenovirus infection of TRBMEC cells. Briefly, TRBMEC cells are directly infected with an adenovirus containing zacrp3 or the parental adenovirus strain. The virus is added at various multiplicities of infection (moi 500, 1,000 and 5,000). Cells are incubated at 37° C., 5% $CO_2$ for 43 hours. Following infection, the adenovirus-infected cells are challenged with TNF (1 ng/ml) for four hours. VCAM expression is measured as described above. Inhibition of VCAM-1 expression is about 13% at moi 5000, about 5% at moi 1000 and no effect is seen at moi 500.

Adenovirus conditioned media is concentrated 10× (Centricon Centrifugal Filtration Unit 5,000K cutoff, Millipore Corp., Bedford, Mass.) according to the manufacturer's instructions followed by heat inactivation at 56° C. for 30 minutes). The concentrated heat inactivated samples are assayed as described above. For VCAM-1 and E-selectin, inhibition is 100%. Similar results are observed when either IL-1 or LPS is used to induce adhesion molecule expression. For ICAM-1, inhibition is reduced to nearly baseline. The experiment is repeated with varying concentrations of zacrp3×2 heat inactivated adenovirus conditioned media. Like zacrp3, acrp3×2 is expected to show complete inhibition at about 5×, 50% inhibition at 2.5× and no inhibition at 0.5×.

A THP-1 monocyte adherence assay according to Ouchi et al., (ibid.) and Cybulsky and Gimbrone, (*Science* 251:788–91, 1991) shows the same results as are seen for VCAM-1 above.

Example 5

Inhibition of Collagen Induced Platelet Aggregation

10×zacrp3×2 adenovirus conditioned media and a parental control are used to measure an effect on collagen induced platelet aggregation. A chronologue aggregometer (Chrono-Log Corp., Haverton, Pa.) is used to measure platelet aggregation in response to type I collagen (Chrono-par #385) either alone or in the presence of zacrp3×2 containing conditioned media.

50 μl of 10×zacrp3×2 adenovirus conditioned media is added to 450 μl of washed platelet suspension. Platelets are gently mixed and collagen is added to a final concentration off 5 μg/mL. Aggregation is measured by recording the percent light transmittance.

For the zacrp3 polypeptide encoded by SEQ ID NO:4, collagen induced platelet aggregation was inhibited by about 80% of collagen control with 1× final concentration zacrp3 containing conditioned media. The parental control showed no inhibition. At 0.5× final concentration, aggregation was inhibited at about 25%. Zacrp3×2 variant is also expected to exhibit similar collagen induced platelet aggregation activity.

In addition, blood is drawn from healthy volunteers into tubes containing sodium citrate, maintained at room temperature and used within four hours of drawing. Whole blood is analyzed for platelet activation using a Chrono-Log 560A Whole Blood Lumi-Aggregometer (Chrono-Log Corp., Haverton, Pa.) according to manufacturer's instructions. For each test point, 500 μl of blood is added to a reaction tube containing a stir bar and 500 μl of isotonic saline containing zsig37 at concentrations from 0 to 20 μg/ml. The mixture is incubated for four minutes followed by platelet activation initiated by the addition of 5 μl of 1 mg/ml cross-linked collagen (Chrono-Log Corp.) to the blood/zsig37 mixture. Inhibition of activation by ADP (final concentration 10 μM), and thrombin (final concentration 1 U/ml) is tested in a similar way.

Example 6

Inhibition of NFkB Using Microvascular Endothelial Cells and a Luciferase NFkB Reporter Assay Microvascular endothelial cells are plated at 50,000 cells/well in 5% FBS/RPMI. The following day, the B2—2 NFkB adenovirus construct is added at a multiplicity of infection of 5,000 in 5% FBS/RPMI. Fifteen hours later, 10× Zacrp3×2 containing Adenovirus conditioned media and parental control media is added to each well. Cells are incubated over night. The following day, the agonists TNF alpha (10 ng/mL), IL-1 beta (10 ng/mL) and LPS (100 ug/mL) are added to one half of the wells and the plate is incubated at 37 degrees C. for 4.5 hours. The plate is then developed using Promega Luciferase Assay Buffer and Luciferase Assay Substrate and luminescence is measured using a luminometer.

For the zacrp3 polypeptide encoded by SEQ ID NO:4, the parental controls had some slight inhibitory effect reducing the maximal TNF response by about 25% and the LPS response by about 10%. No effect was seen on the maximal IL-1 response. The zacrp3 containing conditioned media at a final concentration of 5× reduced the TNF, IL-1, and LPS responses by about 90%. Zacrp3×2 variant is also expected to exhibit similar inhibitory activity.

Moreover, in a preliminary experiment, Zacrp3 conditioned media was tested on cells that were infected with adenovirus luciferase reporter constructs. Conditioned medias tested were from BHK cells, Baculovirus, two samples from TRBME cells, and 293 cells. Reporters used were STAT/SRE, NFkB, and CRE. Preliminary results showed a response in a colon cell line so four colon or small intestine lines were tested. Inhibition of signal relative to conditioned media control was seen in all cell lines. However, this response was not specific for reporter. Chang liver and NIH3T3 cells were also tested to determine if the effect was cell type related. These cell lines also showed inhibition with all reporters.

In order to eliminate the effects of other factors contained in conditioned media, co-infection experiments were done. The same colon or small intestine cell lines as above were infected with zacrp3 adenovirus and a luciferase reporter construct. LoVo cells (human colon) showed inhibition with CRE reporter on three separate experiments. IEC-6 cells (rat small intestine) showed inhibition with both NFkB and STAT/SRE reporters. Chang liver cells showed stimulation with NFkB reporter. All of these samples were tested for zacrp3 by Western analysis but were negative under the Western assay conditions. Zacrp3×2 variant is also expected to exhibit similar inhibitory activity.

NFkB regulates the activation and transcription of genes encoding proteins involved in immune or inflammation responses and cell growth control. (Baldwin, A. S., *Annual Reviews Immunology* 14:649–81, 1996). NFkB binding sites are found in the promoters of many pro-inflammatory genes including TNF, Il-1, and IL-6. Thus, the activation of NFkB may play a critical role in the development of chronic inflammatory diseases such as rheumatoid arthritis or atherosclerosis or in acute situations such as septic shock. LPS stimulation of inflammatory cytokine production results in massive amounts of these proteins, leading ultimately to reduced blood pressure and general organ failure. Inhibitors of NFkB could be used as therapies for these pro-inflammatory conditions. Therapies that are currently used to treat arthritis, for example, such as prednisone or gold compounds, are known to block NFkB. Other conditions such as Alzheimers, involve NFkB activation by amyloid beta peptide. NFkB may also be involved in auto immune disease, such as systemic lupus erythromatus, where an inhibitor of NFkB activation could be therapeutic.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A fusion protein comprising a first portion and a second portion joined by a peptide bond, wherein said first portion comprises a polypeptide of SEQ ID NO:2 or comprises amino acid residues 23–319 of SEQ ID NO:2; and wherein said second portion comprises another polypeptide.

2. An isolated nucleic acid molecule encoding a polypeptide wherein the encoded polypeptide comprises amino acid residues 23–319 of SEQ ID NO:2.

3. The isolated nucleic acid molecule of claim 2 wherein the encoded polypeptide comprises SEQ ID NO:2.

4. An isolated nucleic acid molecule comprising nucleotides 67–957 of SEQ ID NO:1.

5. The isolated nucleic acid molecule of claim 4 wherein the nucleic acid molecule comprises SEQ ID NO:1.

6. An isolated polynucleotide encoding a fusion protein comprising a first portion and a second portion joined by a peptide bond, wherein said first portion comprises a polypeptide of SEQ ID NO:2 or comprises amino acid residues 23–319 of SEQ ID NO:2; and wherein said second portion comprises another polypeptide.

7. The isolated polynucleotide encoding a fusion protein of claim 6 wherein the first portion consists of a polypeptide of SEQ ID NO:2 or comprises amino acid residues 23–319 of SEQ ID NO:2.

8. An expression vector comprising the following operably linked elements:
   a transcription promoter;
   a DNA segment encoding a polypeptide wherein the encoded polypeptide comprises amino acid residues 23–319 of SEQ ID NO:2; and
   a transcription terminator.

9. A cultured cell into which has been introduced an expression vector according to claim 8 wherein said cell expresses said polypeptide encoded by said DNA segment.

10. A method of producing a polypeptide comprising:
    culturing a cell into which has been introduced an expression vector according to claim 8;
    whereby said cell expresses said polypeptide encoded by said DNA segment; and
    recovering said expressed polypeptide.

11. The expression vector of claim 8 wherein the encoded polypeptide comprises SEQ ID NO:2.

* * * * *

SEQUENCE LISTING

```
<160> NUMBER OF SEQ ID NOS: 23

<210> SEQ ID NO 1
<211> LENGTH: 957
<212> TYPE: DNA
<213> ORGANISM: Homo sapiens
<220> FEATURE:
<221> NAME/KEY: CDS
<222> LOCATION: (1)...(957)

<400> SEQUENCE: 1 atg ctt tgg agg cag ctc atc tat tgg caa ctg ctg gct ttg ttt ttc        48
Met Leu Trp Arg Gln Leu Ile Tyr Trp Gln Leu Leu Ala Leu Phe Phe
 1               5                  10                  15 ctc cct ttt tgc ctg tgt caa gat gaa tac atg gag gtg agc gga aga        96
Leu Pro Phe Cys Leu Cys Gln Asp Glu Tyr Met Glu Val Ser Gly Arg
                20                  25                  30 act aat aaa gtg gtg gca aga ata gtg caa agc cac cag cag act ggc       144
Thr Asn Lys Val Val Ala Arg Ile Val Gln Ser His Gln Gln Thr Gly
            35                  40                  45 cgt agc ggc tcc agg agg gag aaa gtg aga gag cgg agc cat cct aaa       192
Arg Ser Gly Ser Arg Arg Glu Lys Val Arg Glu Arg Ser His Pro Lys
        50                  55                  60 act ggg act gtg gat aat aac act tct aca gac cta aaa tcc ctg aga       240
Thr Gly Thr Val Asp Asn Asn Thr Ser Thr Asp Leu Lys Ser Leu Arg
 65                  70                  75                  80 cca gat gag cta ccg cac ccc gag gta gat gac cta gcc cag atc acc       288
Pro Asp Glu Leu Pro His Pro Glu Val Asp Asp Leu Ala Gln Ile Thr
                85                  90                  95 aca ttc tgg ggc cag tct cca caa acc gga gga cta ccc cca gac tgc       336
Thr Phe Trp Gly Gln Ser Pro Gln Thr Gly Gly Leu Pro Pro Asp Cys
            100                 105                 110 agt aag tgt tgt cat gga gac tac agc ttt cga ggc tac caa ggc ccc       384
Ser Lys Cys Cys His Gly Asp Tyr Ser Phe Arg Gly Tyr Gln Gly Pro
        115                 120                 125 cct ggg cca ccg ggc cct cct ggc att cca gga aac cat gga aac aat       432
Pro Gly Pro Pro Gly Pro Pro Gly Ile Pro Gly Asn His Gly Asn Asn
    130                 135                 140 ggc aac aat gga gcc act ggt cat gaa gga gcc aaa ggt gag aag ggc       480
Gly Asn Asn Gly Ala Thr Gly His Glu Gly Ala Lys Gly Glu Lys Gly
145                 150                 155                 160
```

```
gac aaa ggt gac ctg ggg cct cga ggg gag cgg ggg cag cat ggc ccc      528
Asp Lys Gly Asp Leu Gly Pro Arg Gly Glu Arg Gly Gln His Gly Pro
            165                 170                 175 aaa gga gag aag ggc tac ccg ggg att cca cca gaa ctt cag att gca      576
Lys Gly Glu Lys Gly Tyr Pro Gly Ile Pro Pro Glu Leu Gln Ile Ala
        180                 185                 190 ttc atg gct tct ctg gca acc cac ttc agc aat cag aac agt ggg att      624
Phe Met Ala Ser Leu Ala Thr His Phe Ser Asn Gln Asn Ser Gly Ile
    195                 200                 205 atc ttc agc agt gtt gag acc aac att gga aac ttc ttt gat gtc atg      672
Ile Phe Ser Ser Val Glu Thr Asn Ile Gly Asn Phe Phe Asp Val Met
210                 215                 220 act ggt aga ttt ggg gcc cca gta tca ggt gtg tat ttc ttc acc ttc      720
Thr Gly Arg Phe Gly Ala Pro Val Ser Gly Val Tyr Phe Phe Thr Phe
225                 230                 235                 240 agc atg atg aag cat gag gat gtt gag gaa gtg tat gtg tac ctt atg      768
Ser Met Met Lys His Glu Asp Val Glu Glu Val Tyr Val Tyr Leu Met
            245                 250                 255 cac aat ggc aac aca gtc ttc agc atg tac agc tat gaa atg aag ggc      816
His Asn Gly Asn Thr Val Phe Ser Met Tyr Ser Tyr Glu Met Lys Gly
        260                 265                 270 aaa tca gat aca tcc agc aat cat gct gtg ctg aag cta gcc aaa ggg      864
Lys Ser Asp Thr Ser Ser Asn His Ala Val Leu Lys Leu Ala Lys Gly
    275                 280                 285 gat gag gtt tgg ctg cga atg ggc aat ggc gct ctc cat ggg gac cac      912
Asp Glu Val Trp Leu Arg Met Gly Asn Gly Ala Leu His Gly Asp His
290                 295                 300 caa cgc ttc tcc acc ttt gca gga ttc ctg ctc ttt gaa act aag          957
Gln Arg Phe Ser Thr Phe Ala Gly Phe Leu Leu Phe Glu Thr Lys
305                 310                 315

<210> SEQ ID NO 2
<211> LENGTH: 319
<212> TYPE: PRT
<213> ORGANISM: Homo sapiens

<400> SEQUENCE: 2

Met Leu Trp Arg Gln Leu Ile Tyr Trp Gln Leu Leu Ala Leu Phe Phe
1               5                   10                  15

Leu Pro Phe Cys Leu Cys Gln Asp Glu Tyr Met Glu Val Ser Gly Arg
            20                  25                  30

Thr Asn Lys Val Val Ala Arg Ile Val Gln Ser His Gln Gln Thr Gly
        35                  40                  45

Arg Ser Gly Ser Arg Arg Glu Lys Val Arg Glu Arg Ser His Pro Lys
    50                  55                  60

Thr Gly Thr Val Asp Asn Asn Thr Ser Thr Asp Leu Lys Ser Leu Arg
65                  70                  75                  80

Pro Asp Glu Leu Pro His Pro Glu Val Asp Asp Leu Ala Gln Ile Thr
                85                  90                  95

Thr Phe Trp Gly Gln Ser Pro Gln Thr Gly Gly Leu Pro Pro Asp Cys
            100                 105                 110

Ser Lys Cys Cys His Gly Asp Tyr Ser Phe Arg Gly Tyr Gln Gly Pro
        115                 120                 125

Pro Gly Pro Pro Gly Pro Pro Gly Ile Pro Gly Asn His Gly Asn Asn
    130                 135                 140

Gly Asn Asn Gly Ala Thr Gly His Glu Gly Ala Lys Gly Glu Lys Gly
145                 150                 155                 160

Asp Lys Gly Asp Leu Gly Pro Arg Gly Glu Arg Gly Gln His Gly Pro
```

-continued

```
                    165                 170                 175
Lys Gly Glu Lys Gly Tyr Pro Gly Ile Pro Pro Glu Leu Gln Ile Ala
                180                 185                 190

Phe Met Ala Ser Leu Ala Thr His Phe Ser Asn Gln Asn Ser Gly Ile
            195                 200                 205

Ile Phe Ser Ser Val Glu Thr Asn Ile Gly Asn Phe Phe Asp Val Met
        210                 215                 220

Thr Gly Arg Phe Gly Ala Pro Val Ser Gly Val Tyr Phe Thr Phe
225                 230                 235                 240

Ser Met Met Lys His Glu Asp Val Glu Val Tyr Val Tyr Leu Met
                245                 250                 255

His Asn Gly Asn Thr Val Phe Ser Met Tyr Ser Tyr Glu Met Lys Gly
                260                 265                 270

Lys Ser Asp Thr Ser Ser Asn His Ala Val Leu Lys Leu Ala Lys Gly
                275                 280                 285

Asp Glu Val Trp Leu Arg Met Gly Asn Gly Ala Leu His Gly Asp His
            290                 295                 300

Gln Arg Phe Ser Thr Phe Ala Gly Phe Leu Leu Phe Glu Thr Lys
305                 310                 315
```

<210> SEQ ID NO 3
<211> LENGTH: 1696
<212> TYPE: DNA
<213> ORGANISM: Homo sapiens
<220> FEATURE:
<221> NAME/KEY: CDS
<222> LOCATION: (69)...(806)

<400> SEQUENCE: 3

```
cccgaggaga ccacgctcct ggagctctgc tgtcttctca gggagactct gaggctctgt      60 tgagaatc atg ctt tgg agg cag ctc atc tat tgg caa ctg ctg gct ttg     110
         Met Leu Trp Arg Gln Leu Ile Tyr Trp Gln Leu Leu Ala Leu
           1               5                  10 ttt ttc ctc cct ttt tgc ctg tgt caa gat gaa tac atg gag tct cca     158
Phe Phe Leu Pro Phe Cys Leu Cys Gln Asp Glu Tyr Met Glu Ser Pro
 15                  20                  25                  30 caa acc gga gga cta ccc cca gac tgc agt aag tgt tgt cat gga gac     206
Gln Thr Gly Gly Leu Pro Pro Asp Cys Ser Lys Cys Cys His Gly Asp
             35                  40                  45 tac agc ttt cga ggc tac caa ggc ccc cct ggg cca ccg ggc cct cct     254
Tyr Ser Phe Arg Gly Tyr Gln Gly Pro Pro Gly Pro Pro Gly Pro Pro
         50                  55                  60 ggc att cca gga aac cat gga aac aat ggc aac aat gga gcc act ggt     302
Gly Ile Pro Gly Asn His Gly Asn Asn Gly Asn Asn Gly Ala Thr Gly
     65                  70                  75 cat gaa gga gcc aaa ggt gag aag ggc gac aaa ggt gac ctg ggg cct     350
His Glu Gly Ala Lys Gly Glu Lys Gly Asp Lys Gly Asp Leu Gly Pro
 80                  85                  90 cga ggg gag cgg ggg cag cat ggc ccc aaa gga gag aag ggc tac ccg     398
Arg Gly Glu Arg Gly Gln His Gly Pro Lys Gly Glu Lys Gly Tyr Pro
 95                 100                 105                 110 ggg att cca cca gaa ctt cag att gca ttc atg gct tct ctg gca acc     446
Gly Ile Pro Pro Glu Leu Gln Ile Ala Phe Met Ala Ser Leu Ala Thr
             115                 120                 125 cac ttc agc aat cag aac agt ggg att atc ttc agc agt gtt gag acc     494
His Phe Ser Asn Gln Asn Ser Gly Ile Ile Phe Ser Ser Val Glu Thr
         130                 135                 140 aac att gga aac ttc ttt gat gtc atg act ggt aga ttt ggg gcc cca     542
```

```
Asn Ile Gly Asn Phe Phe Asp Val Met Thr Gly Arg Phe Gly Ala Pro
         145                 150                 155 gta tca ggt gtg tat ttc ttc acc ttc agc atg atg aag cat gag gat       590
Val Ser Gly Val Tyr Phe Phe Thr Phe Ser Met Met Lys His Glu Asp
    160                 165                 170 gtt gag gaa gtg tat gtg tac ctt atg cac aat ggc aac aca gtc ttc       638
Val Glu Glu Val Tyr Val Tyr Leu Met His Asn Gly Asn Thr Val Phe
175                 180                 185                 190 agc atg tac agc tat gaa atg aag ggc aaa tca gat aca tcc agc aat       686
Ser Met Tyr Ser Tyr Glu Met Lys Gly Lys Ser Asp Thr Ser Ser Asn
                195                 200                 205 cat gct gtg ctg aag cta gcc aaa ggg gat gag gtt tgg ctg cga atg       734
His Ala Val Leu Lys Leu Ala Lys Gly Asp Glu Val Trp Leu Arg Met
            210                 215                 220 ggc aat ggc gct ctc cat ggg gac cac caa cgc ttc tcc acc ttt gca       782
Gly Asn Gly Ala Leu His Gly Asp His Gln Arg Phe Ser Thr Phe Ala
        225                 230                 235 gga ttc ctg ctc ttt gaa act aag taaatatatg actagaatag ctccactttg      836
Gly Phe Leu Leu Phe Glu Thr Lys
    240                 245 gggaagactt gtagctgagc tgatttgtta cgatctgagg aacattaaag ttgagggttt     896
tacattgctg tattcaaaaa attattggtt gcaatgttgt tcacgctaca ggtacaccaa     956
taatgttgga caattcaggg gctcagaaga atcaaccaca aaatagtctt ctcagatgac    1016
cttgactaat atactcagca tctttatcac tcttccttg gcacctaaaa gataattctc    1076
ctctgacgca ggttggaaat attttttct atcacagaag tcatttgcaa agaattttga    1136
ctactctgct tttaatttaa taccagtttt caggaacccc tgaagtttta agttcattat    1196
tctttataac atttgagaga atcggatgta gtgatatgac agggctgggg caagaacagg    1256
ggcactagct gccttattag ctaatttagt gccctccgtg ttcagcttag cctttgaccc    1316
tttccttttg atccacaaaa tacattaaaa ctctgaattc acatacaatg ctattttaaa    1376
gtcaatagat tttagctata aagtgcttga ccagtaatgt ggttgtaatt ttgtgtatgt    1436 tccccccacat cgcccccaac ttcggatgtg gggtcaggag gttgaggttc actattaaca    1496
aatgtcataa atatctcata gaggtacagt gccaatagat attcaaatgt tgcatgttga    1556
ccagagggat tttatatctg aagaacatac actattaata aataccttag agaaagattt    1616
tgacctggct ttagataaaa ctgtggcaag aaaaatgtaa tgagcaatat atggaaataa    1676 acacccttt gttaaagata                                                 1696

<210> SEQ ID NO 4
<211> LENGTH: 219
<212> TYPE: DNA
<213> ORGANISM: Homo sapiens
<220> FEATURE:
<221> NAME/KEY: CDS
<222> LOCATION: (1)...(219)

<400> SEQUENCE: 4 gtg agc gga aga act aat aaa gtg gtg gca aga ata gtg caa agc cac        48
Val Ser Gly Arg Thr Asn Lys Val Val Ala Arg Ile Val Gln Ser His
1               5                  10                  15 cag cag act ggc cgt agc ggc tcc agg agg gag aaa gtg aga gag cgg        96
Gln Gln Thr Gly Arg Ser Gly Ser Arg Arg Glu Lys Val Arg Glu Arg
            20                  25                  30 agc cat cct aaa act ggg act gtg gat aat aac act tct aca gac cta       144
Ser His Pro Lys Thr Gly Thr Val Asp Asn Asn Thr Ser Thr Asp Leu
        35                  40                  45
```

```
aaa tcc ctg aga cca gat gag cta ccg cac ccc gag gta gat gac cta        192
Lys Ser Leu Arg Pro Asp Glu Leu Pro His Pro Glu Val Asp Asp Leu
 50              55                  60 gcc cag atc acc aca ttc tgg ggc cag                                    219
Ala Gln Ile Thr Thr Phe Trp Gly Gln
 65              70
```

<210> SEQ ID NO 5
<211> LENGTH: 436
<212> TYPE: DNA
<213> ORGANISM: Homo sapiens
<220> FEATURE:
<221> NAME/KEY: CDS
<222> LOCATION: (1)...(436)

<400> SEQUENCE: 5

```
ctg gct ttg ttt ttc ctc cct ttt tgc ctg tgt caa gat gaa tac atg         48
Leu Ala Leu Phe Phe Leu Pro Phe Cys Leu Cys Gln Asp Glu Tyr Met
 1               5                  10                  15 gag gtg agc gga aga act aat aaa gtg gtg gca aga ata gtg caa agc         96
Glu Val Ser Gly Arg Thr Asn Lys Val Val Ala Arg Ile Val Gln Ser
             20                  25                  30 cac cag cag act ggc cgt agc ggc tcc agg agg gag aaa gtg aga gag        144
His Gln Gln Thr Gly Arg Ser Gly Ser Arg Arg Glu Lys Val Arg Glu
         35                  40                  45 cgg agc cat cct aaa act ggg act gtg gat aat aac act tct aca gac        192
Arg Ser His Pro Lys Thr Gly Thr Val Asp Asn Asn Thr Ser Thr Asp
     50                  55                  60 cta aaa tcc ctg aga cca gat gag cta ccg cac ccc gag gta gat gac        240
Leu Lys Ser Leu Arg Pro Asp Glu Leu Pro His Pro Glu Val Asp Asp
 65                  70                  75                  80 cta gcc cag atc acc aca ttc tgg ggc cag tct cca caa acc gga gga        288
Leu Ala Gln Ile Thr Thr Phe Trp Gly Gln Ser Pro Gln Thr Gly Gly
                 85                  90                  95 cta ccc cca gac tgc agt aag tgt tgt cat gga gac tac agc ttt cga        336
Leu Pro Pro Asp Cys Ser Lys Cys Cys His Gly Asp Tyr Ser Phe Arg
            100                 105                 110 ggc tac caa ggc ccc cct ggg cca ccg ggc cct cct ggc att cca gga        384
Gly Tyr Gln Gly Pro Pro Gly Pro Pro Gly Pro Pro Gly Ile Pro Gly
        115                 120                 125 aac cat gga aac aat ggc aac aat gga gcc act ggt cat gaa gga gcc        432
Asn His Gly Asn Asn Gly Asn Asn Gly Ala Thr Gly His Glu Gly Ala
    130                 135                 140 aaa g                                                                  436
Lys
145
```

<210> SEQ ID NO 6
<211> LENGTH: 391
<212> TYPE: PRT
<213> ORGANISM: Homo sapiens

<400> SEQUENCE: 6

```
Met Gly Tyr Pro Glu Val Glu Arg Glu Leu Leu Pro Ala Ala Ala
 1               5                  10                  15

Pro Arg Glu Arg Gly Ser Gln Gly Cys Gly Cys Gly Gly Ala Pro Ala
             20                  25                  30

Arg Ala Gly Glu Gly Asn Ser Cys Leu Leu Phe Leu Gly Phe Phe Gly
         35                  40                  45

Leu Ser Leu Ala Leu His Leu Leu Thr Leu Cys Cys Tyr Leu Glu Leu
     50                  55                  60
```

-continued

```
Arg Ser Glu Leu Arg Arg Glu Arg Gly Ala Glu Ser Arg Leu Gly Gly
 65                  70                  75                  80

Ser Gly Thr Pro Gly Thr Ser Gly Thr Leu Ser Ser Leu Gly Gly Leu
                 85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Pro Asp Glu Lys
    130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Pro Gly Pro Pro Gly Pro Pro Gly
    210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
        355                 360                 365

Ile Ser Ile Asn Met Ser Lys His Thr Phe Phe Gly Ala Ile Arg
    370                 375                 380

Leu Gly Glu Ala Pro Ala Ser
385                 390
```

<210> SEQ ID NO 7
<211> LENGTH: 957
<212> TYPE: DNA
<213> ORGANISM: Artificial Sequence
<220> FEATURE:
<223> OTHER INFORMATION: Degenerate polynucleotide sequence encoding a
      zacrp3x2 polypeptide of SEQ ID NO:2.
<220> FEATURE:
<221> NAME/KEY: misc_feature
<222> LOCATION: (1)...(957)
<223> OTHER INFORMATION: n = A, T, C or G

<400> SEQUENCE: 7

```
atgytntggm gncarytnat htaytggcar ytnytngcny tnttyttyyt nccnttytgy      60 ytntgycar

```
<223> OTHER INFORMATION: Xaa is any amino acid residue
<220> FEATURE:
<221> NAME/KEY: VARIANT
<222> LOCATION: (31)...(31)
<223> OTHER INFORMATION: Xaa is phenylalanine or tyrosine

<400> SEQUENCE: 8

Phe Xaa Xaa Xaa Xaa Xaa Xaa Xaa Xaa Xaa Xaa Xaa Xaa Xaa Xaa Xaa
 1               5                   10                  15

Xaa Xaa Phe Xaa Xaa Xaa Xaa Xaa Gly Xaa Tyr Xaa Phe Xaa Xaa
            20                  25                  30

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide primer ZC21,195

<400> SEQUENCE: 9
gaggagacca taacccccga cag                                          23

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide primer ZC21,196

<400> SEQUENCE: 10
catagctccc accacacgat ttt                                          23

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide primer ZC14,063

<400> SEQUENCE: 11
caccagacat aatagctgac agact                                        25

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide primer ZC17,574

<400> SEQUENCE: 12
ggtrttgctc agcatgcaca c                                            21

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide primer ZC17,600

<400> SEQUENCE: 13
catgtaggcc atgaggtcca ccac                                         24

<210> SEQ ID NO 14
<211> LENGTH: 84
<212> TYPE: DNA
<213> ORGANISM: Artificial Sequence
```

```
<220> FEATURE:
<223> OTHER INFORMATION: Oligonucleotide primer ZC23,989

<400> SEQUENCE: 14
tcactaccgg gcgtattttt tgagttatcg agattttcag gagctaagga agctaaaatg      60
gccaagttga ccagtgccgt tccg                                             84

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer ZC23,899

<400> SEQUENCE: 15
actgctggct ttgtttttcc tccc                                             24

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide primer ZC23,898

<400> SEQUENCE: 16
ccttctcacc tttggctcct tca                                              23

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide primer ZC23,899

<400> SEQUENCE: 17
actgctggct ttgtttttcc tccc                                             24

<210> SEQ ID NO 18
<211> LENGTH: 23
<212> TYPE: DNA
<213> ORGANISM: Artificial Sequence
<220> FEATURE:
<223> OTHER INFORMATION: Oligonucleotide primer ZC38,824

<400> SEQUENCE: 18
agggagactc tgaggctctg ttg                                              23

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide primer ZC38,825

<400> SEQUENCE: 19
gctcagctac aagtcttccc caa                                              23

<210> SEQ ID NO 20
<211> LENGTH: 18
<212> TYPE: DNA
<213> ORGANISM: Artificial Sequence
<220> FEATURE:
<223> OTHER INFORMATION: Oligonucleotide primer ZC21,909

<400> SEQUENCE: 20
```

```
catggcccca aaggagag                                                    18

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer ZC20,838

<400> SEQUENCE: 21
aatgttggtc tcaacactgc                                                  20

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide primer ZC21,913

<400> SEQUENCE: 22
tgaccagagg gattttat                                                    18

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide primer ZC21,914

<400> SEQUENCE: 23
ttgccacagt tttatcta                                                    18
```